United States Patent [19]
Walker et al.

[11] Patent Number: 5,564,414
[45] Date of Patent: Oct. 15, 1996

[54] PRESSURIZED AND METERED MEDICATION DOSE COUNTER ON REMOVABLE SLEEVE

[76] Inventors: William F. Walker; Elizabeth M. Walker, both of 6 Arbor Rd., South Burlington, Vt. 05403

[21] Appl. No.: 249,702

[22] Filed: May 26, 1994

[51] Int. Cl.⁶ .......................... A61M 11/00; A62B 7/00; A62B 9/00; B67D 5/26
[52] U.S. Cl. ................ 128/200.23; 128/202.22; 128/205.23; 128/203.12; 222/32; 222/36; 239/71; 239/74
[58] Field of Search .................. 128/200.23, 202.22, 128/205.23, 203.10, 200.14; 222/645–649, 32, 36, 162; 239/71, 74

[56] References Cited

U.S. PATENT DOCUMENTS

| | | | |
|---|---|---|---|
| 4,436,223 | 3/1984 | Wilson | 222/36 |
| 4,817,822 | 4/1989 | Rand et al. | 128/200.23 |
| 5,020,527 | 6/1991 | Dessertine | 128/200.23 |
| 5,349,945 | 9/1994 | Wass et al. | 128/200.23 |
| 5,394,866 | 3/1995 | Ritson et al. | 128/200.23 |

FOREIGN PATENT DOCUMENTS

| | | | |
|---|---|---|---|
| 1389328 | 4/1975 | United Kingdom | A61B 5/00 |
| 2195544 | 4/1988 | United Kingdom | 128/200.23 |
| 8602275 | 4/1986 | WIPO | 128/200.23 |
| 9106334 | 5/1991 | WIPO | 128/200.23 |
| 9209324 | 6/1992 | WIPO | 128/200.23 |
| WO92/15353 | 9/1992 | WIPO | A61M 11/00 |
| WO92/17231 | 10/1992 | WIPO | A61M 11/00 |

*Primary Examiner*—Kimberly L. Asher
*Attorney, Agent, or Firm*—Joseph Scafetta, Jr.

[57] ABSTRACT

A system delivers a number of safe doses from a pressurized and metered medication canister via a dispenser to a patient. The improvement includes a counter device for accurately determining the number of safe doses delivered from the medication canister. Also, a warning device alerts the patient either visually, audibly, mechanically or in a combination thereof about an impending and then a final exhaustion of the number of safe doses delivered from the medication canister. The improved system takes advantage of the patient-actuated movement of the medication canister in the dispenser body to activate either an electronic or a mechanical counter device. Alternatively, the improved system may be patient-activated independently from, but in conjunction with, the dispensing of medication from the canister.

14 Claims, 16 Drawing Sheets

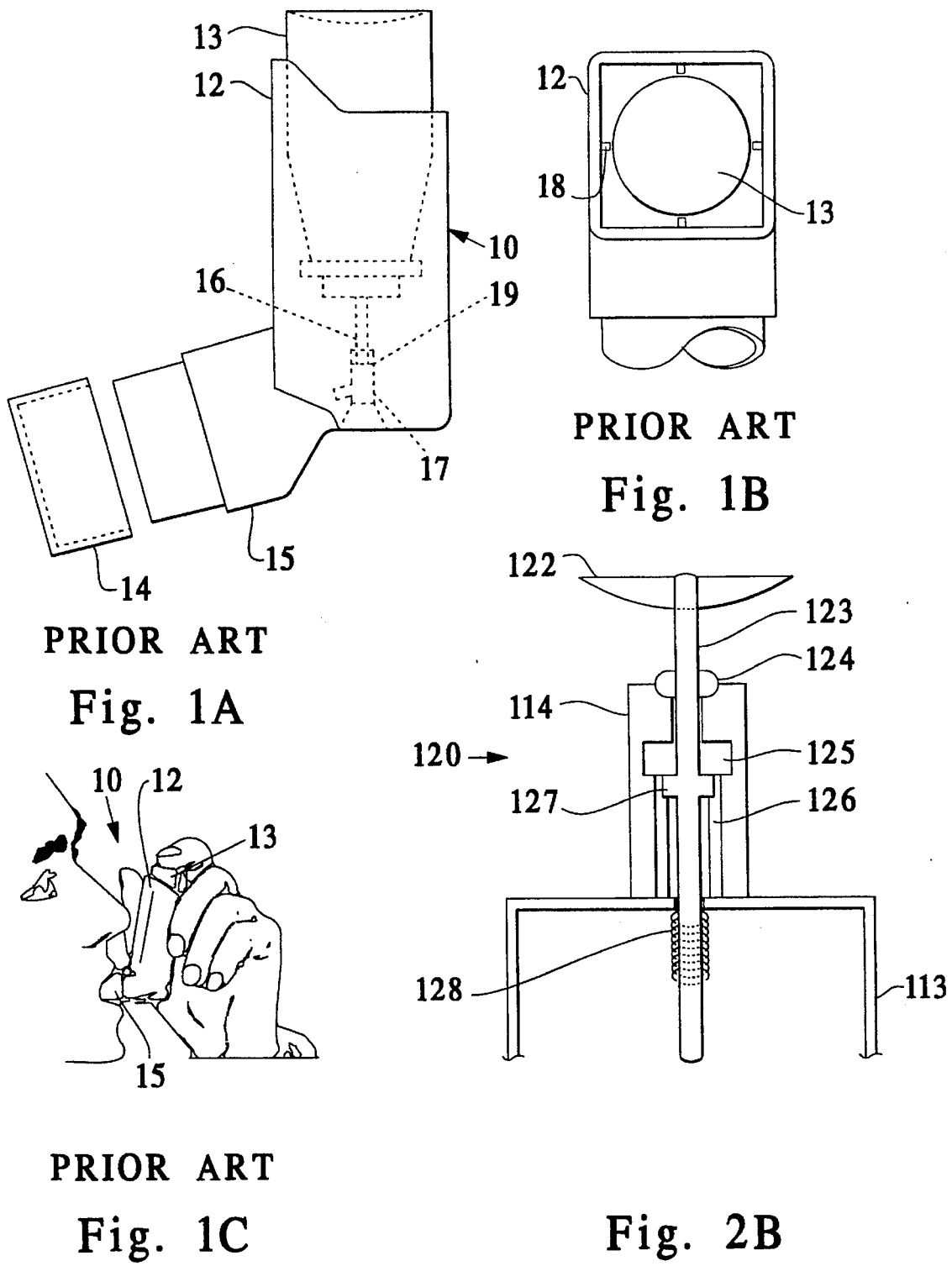

Fig. 3A
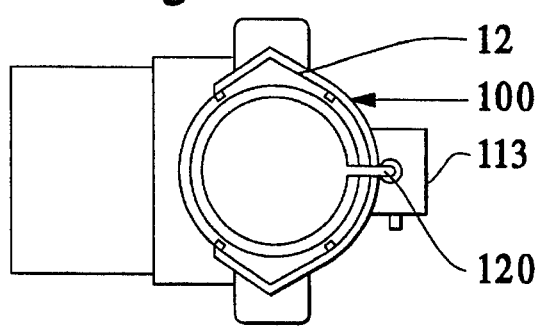
Fig. 3C
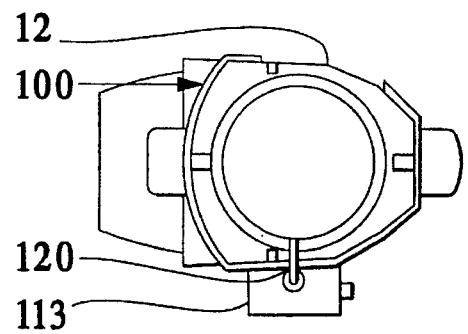
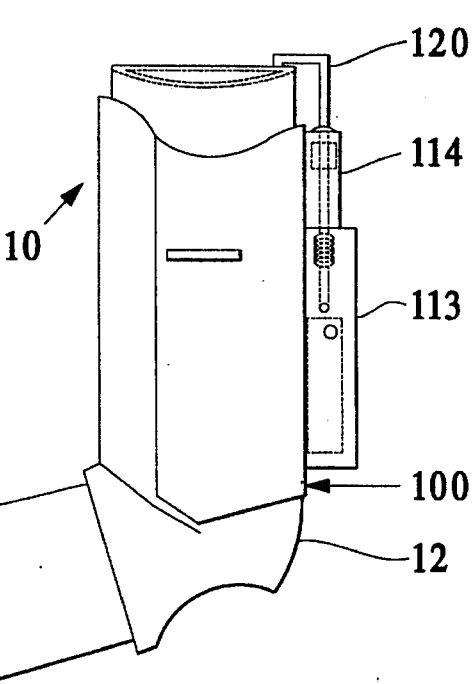
Fig. 3B
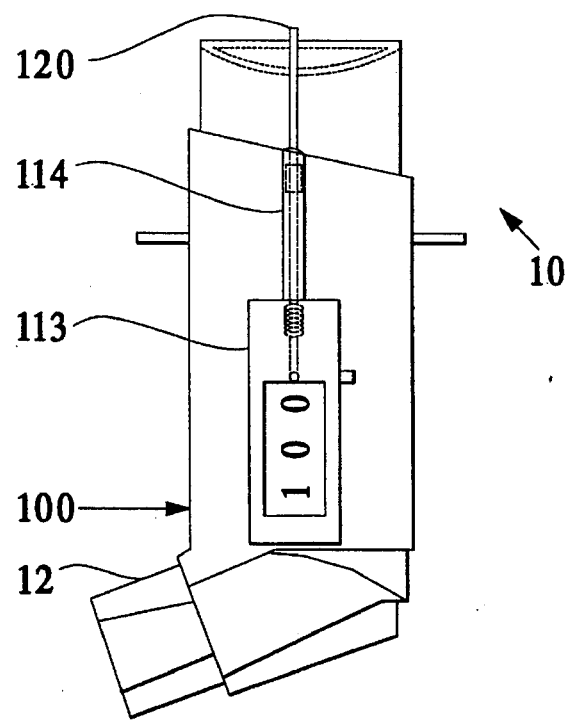
Fig. 3D

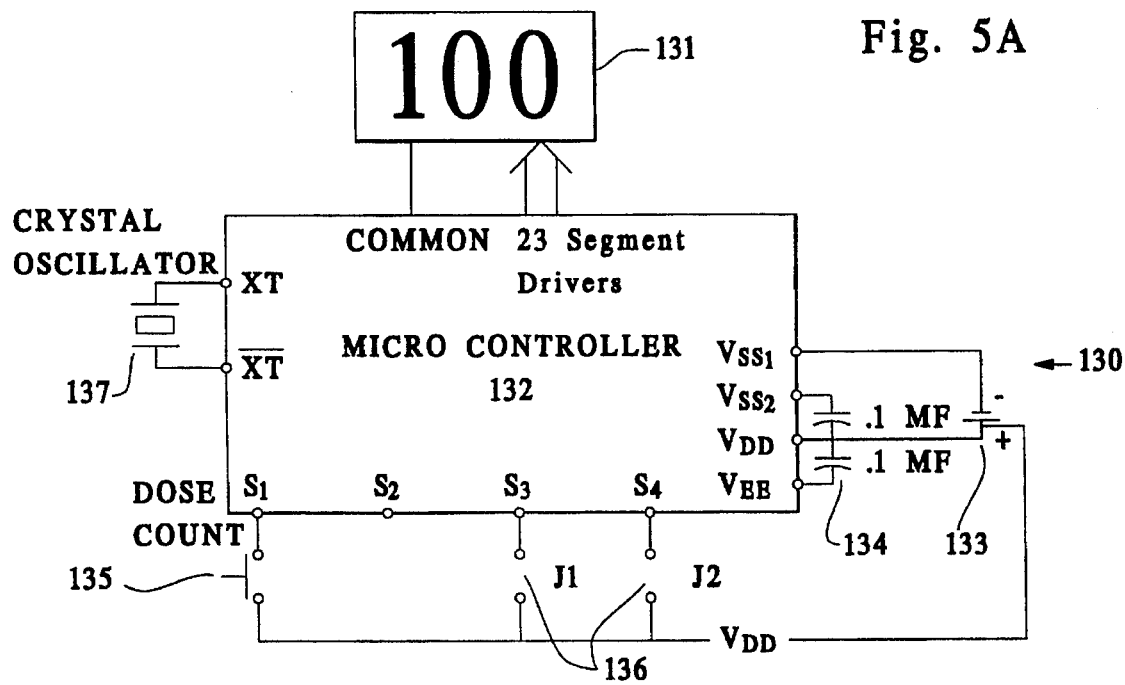
Fig. 5A
Fig. 5B
JUMPER INSTALLATION TABLE
PROGRAM JUMPERS
| PRESET | J1 | J2 |
|---|---|---|
| 100 | 0 | 0 |
| 118 | X | 0 |
| 150 | 0 | X |
| 200 | X | X |
0=No Jumper
X=Jumper Installed
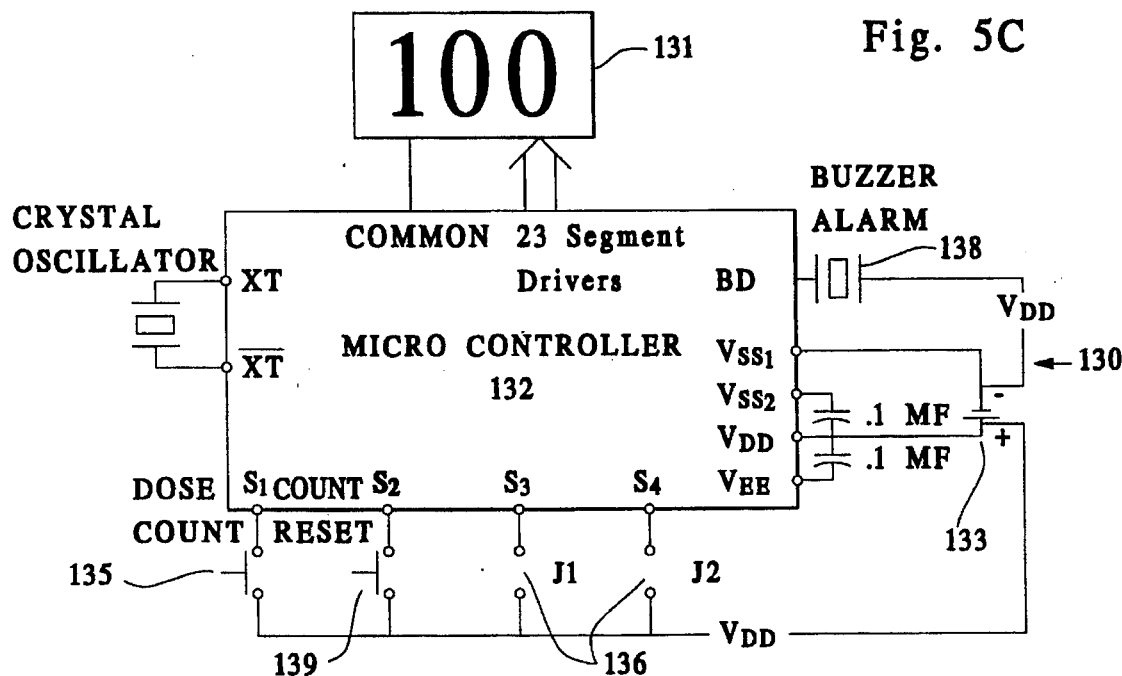
Fig. 5C Fig. 6C
Fig. 6A
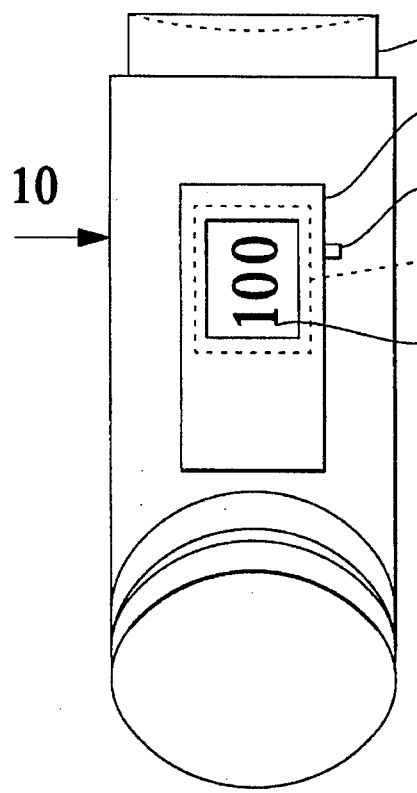
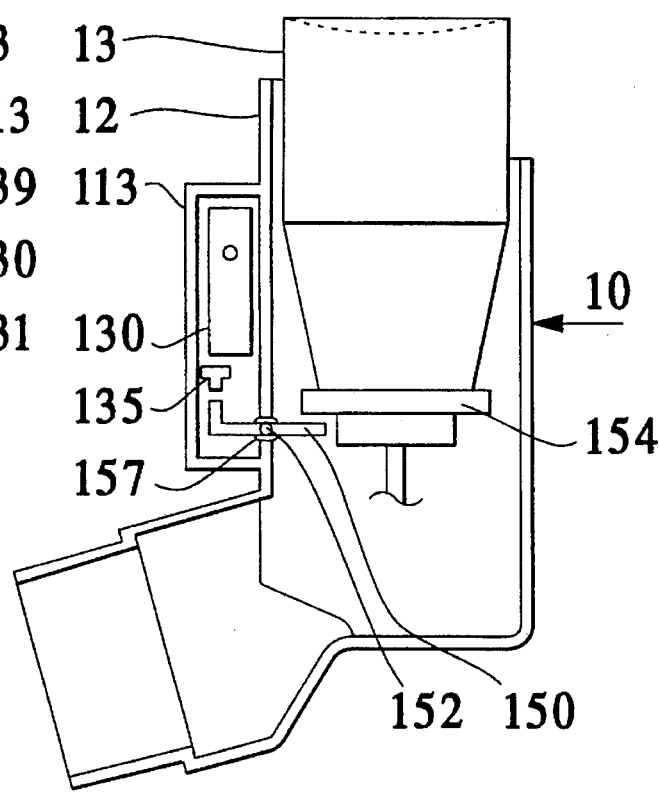
Fig. 6B
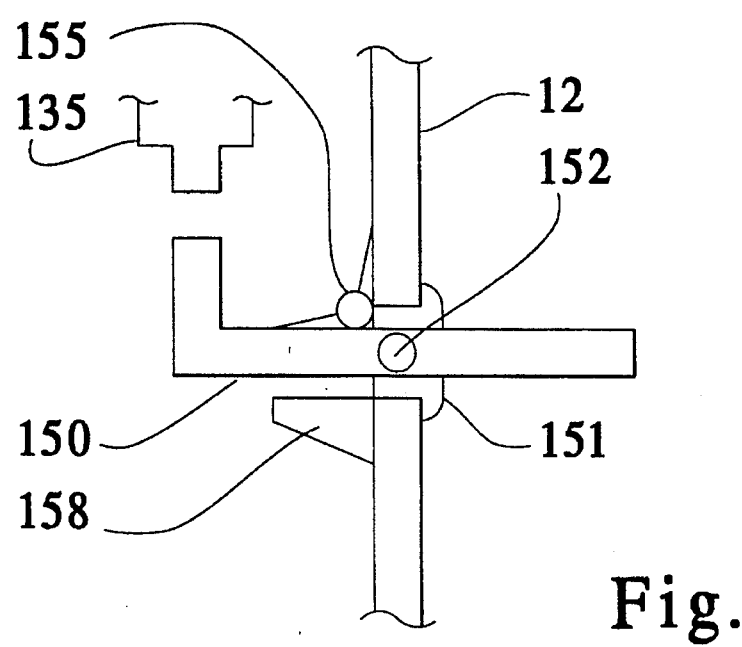

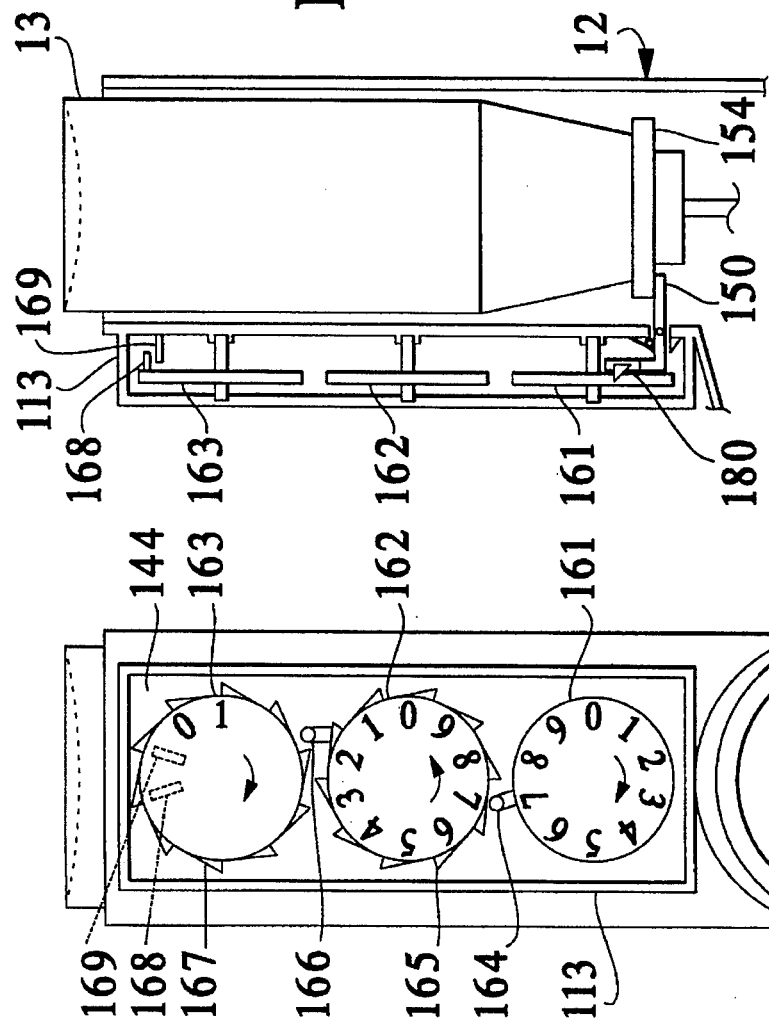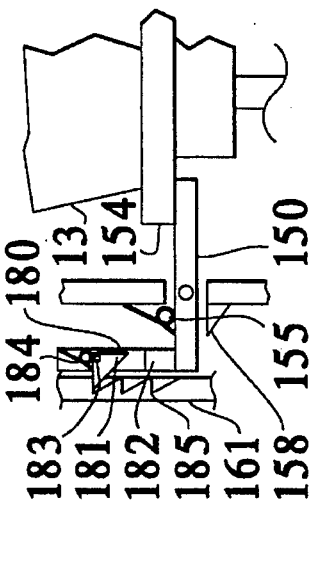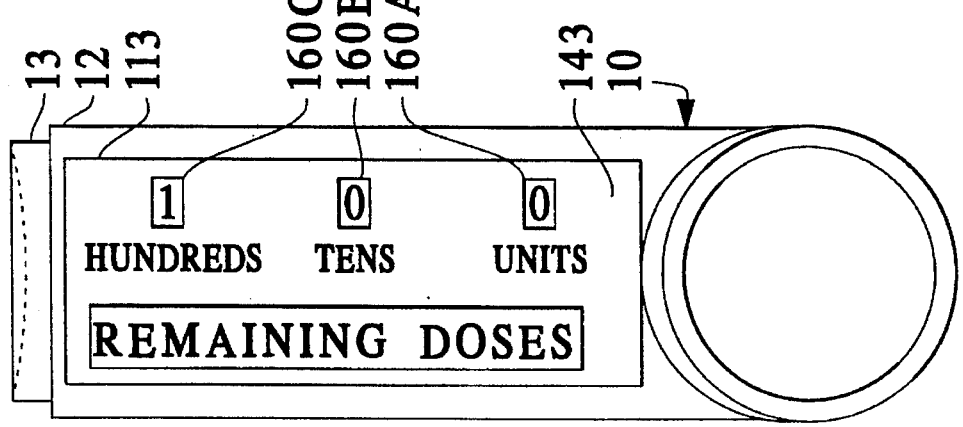

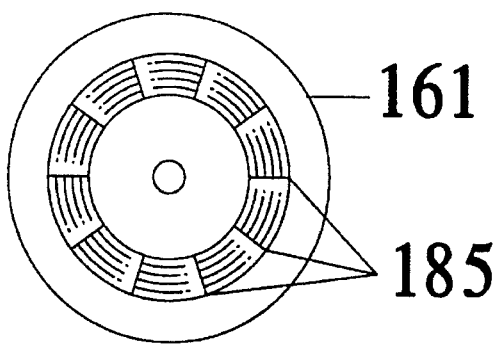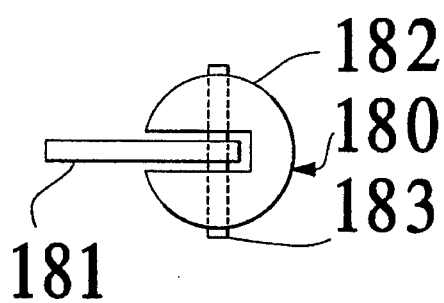
Fig. 7F    Fig. 7E
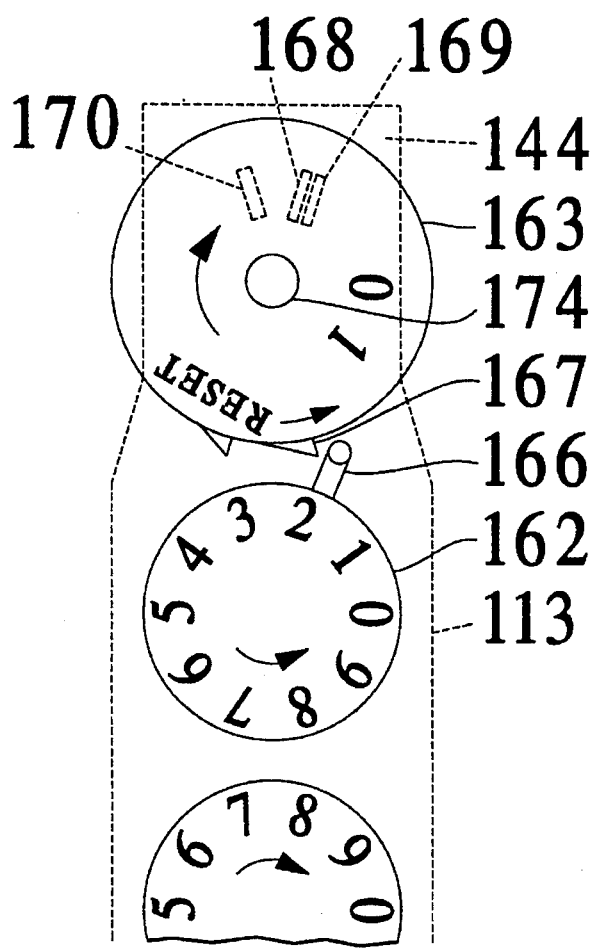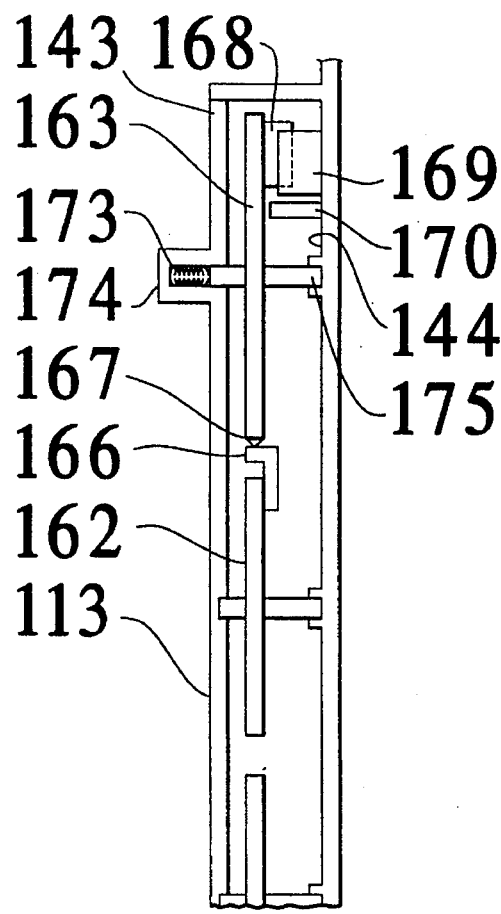
Fig. 7G    Fig. 7H

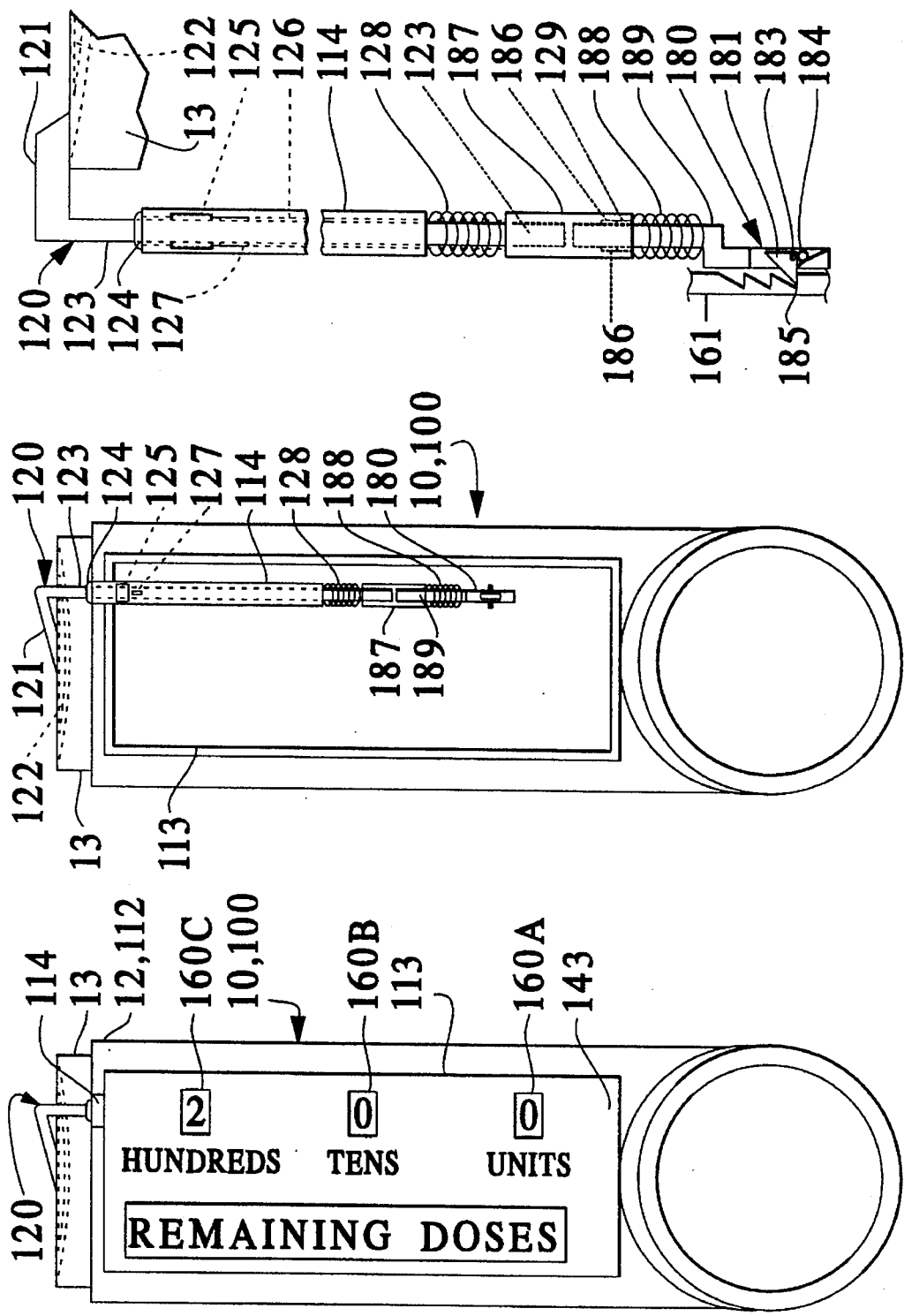

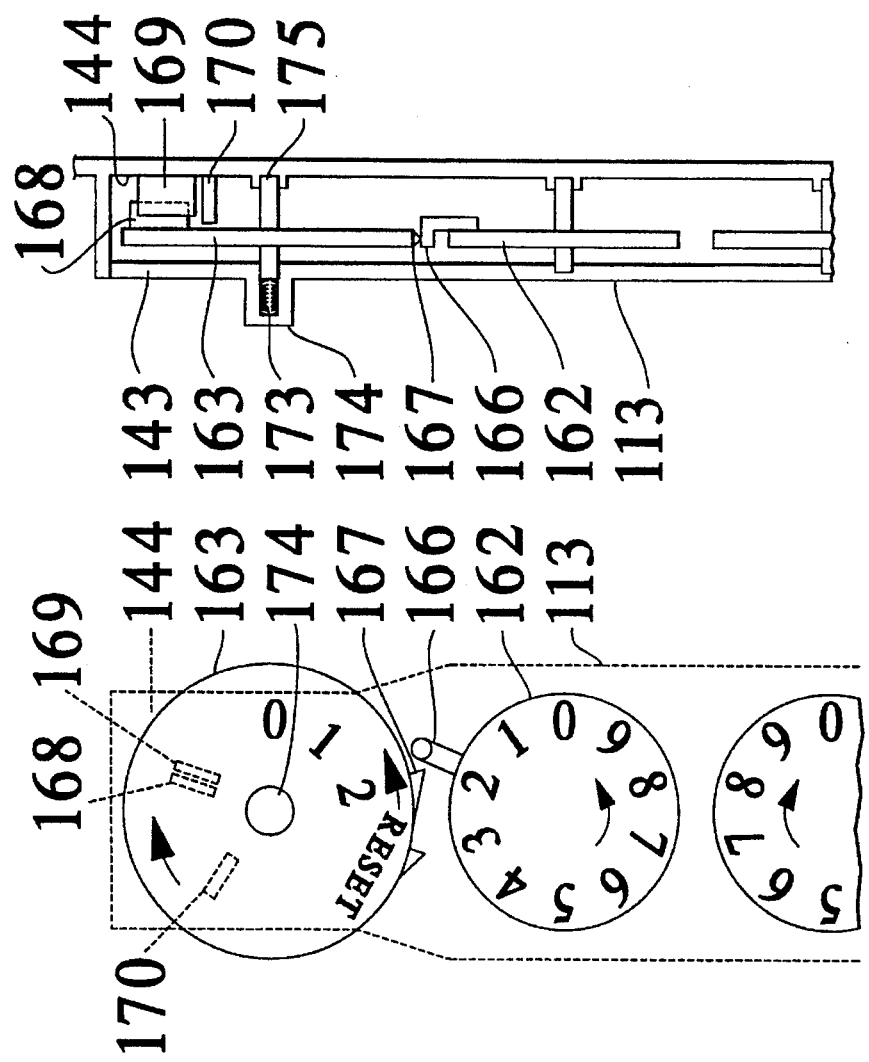
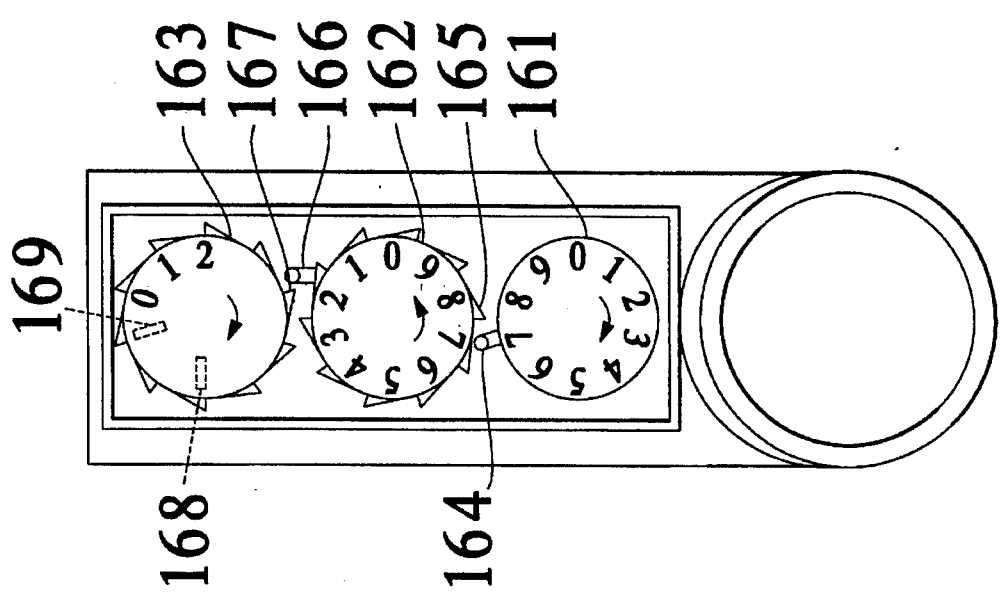
Fig. 8D  Fig. 8E  Fig. 8F

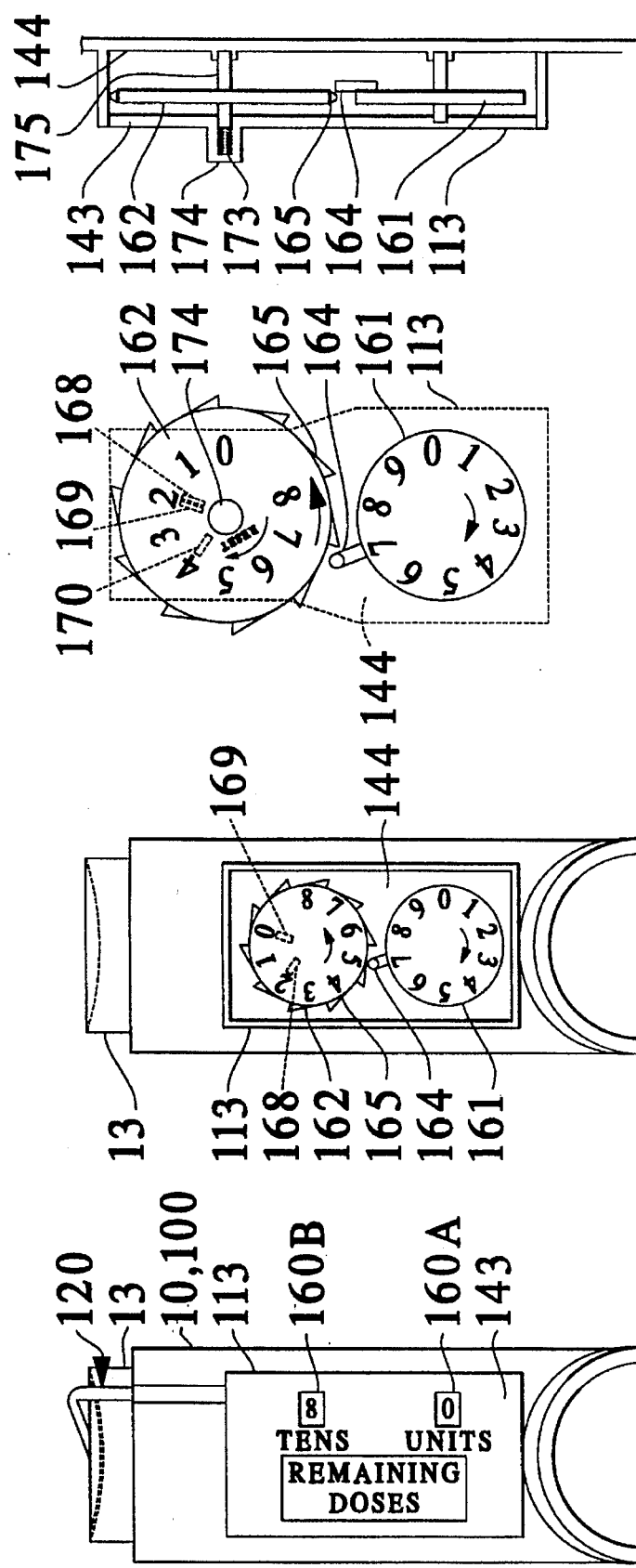

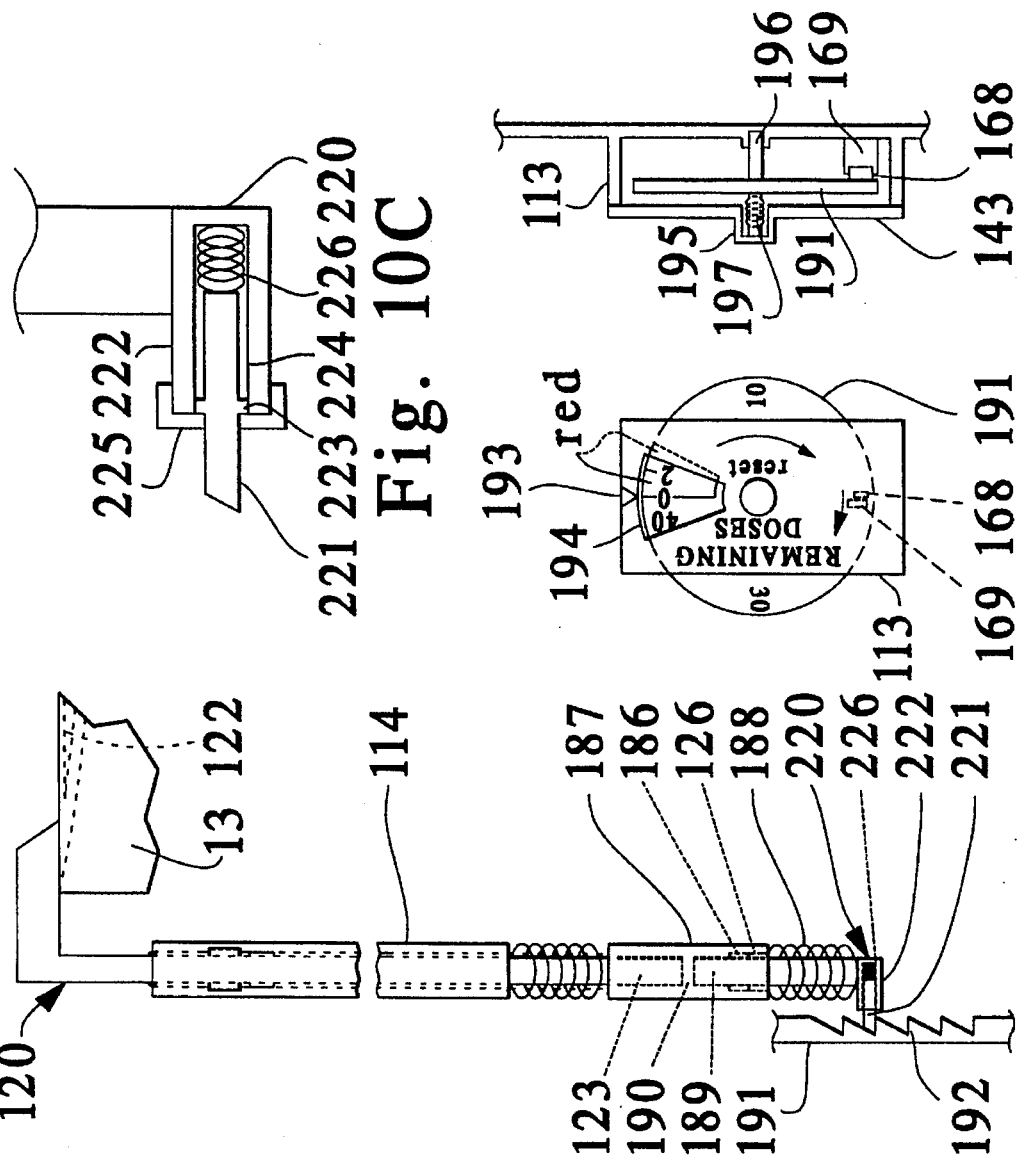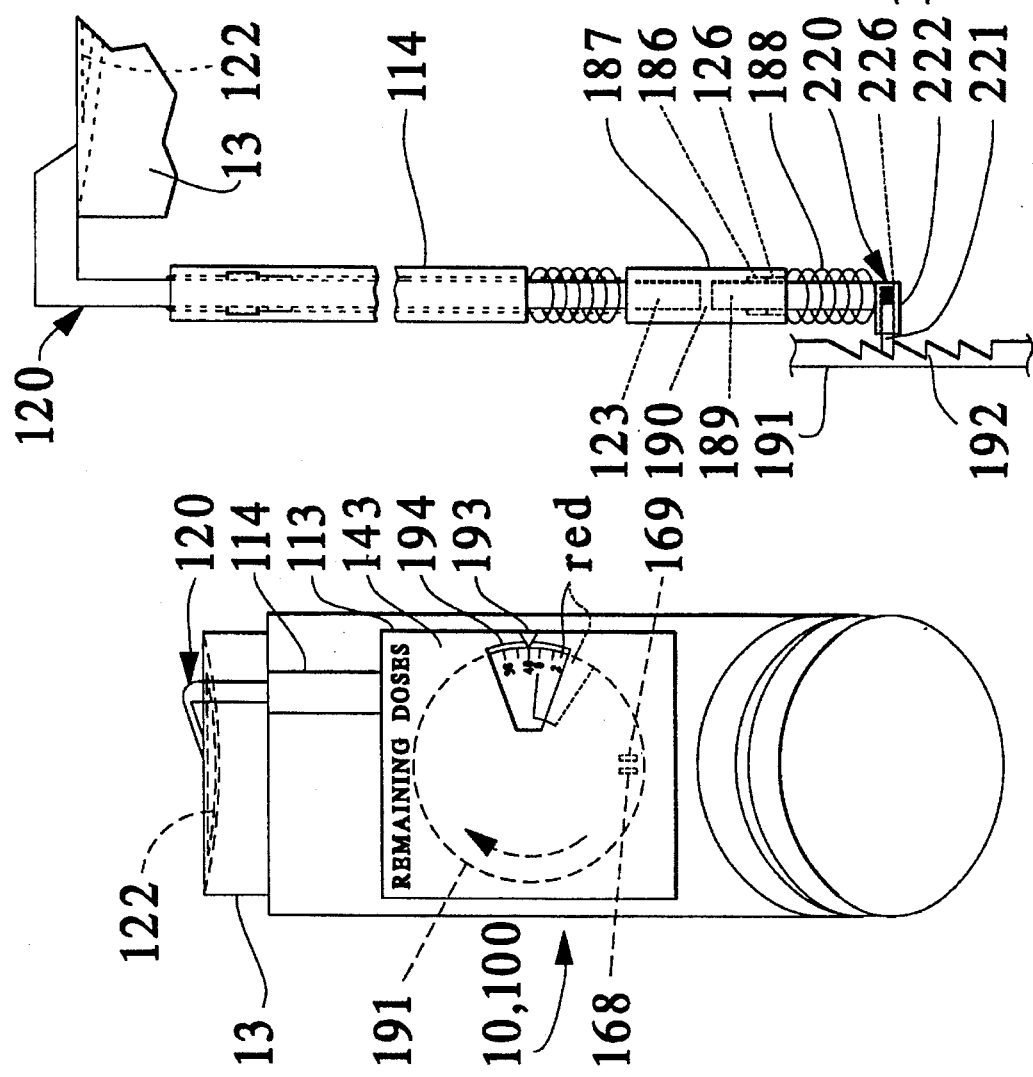

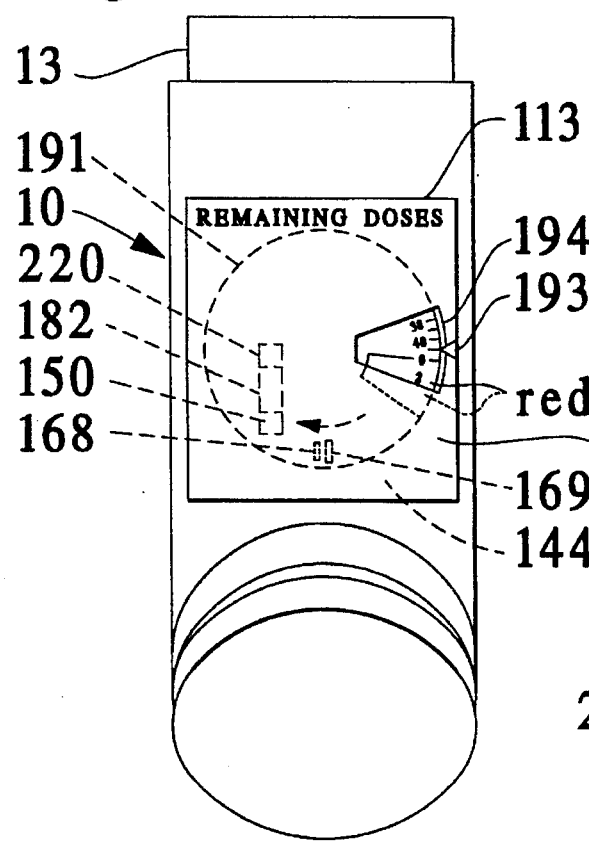
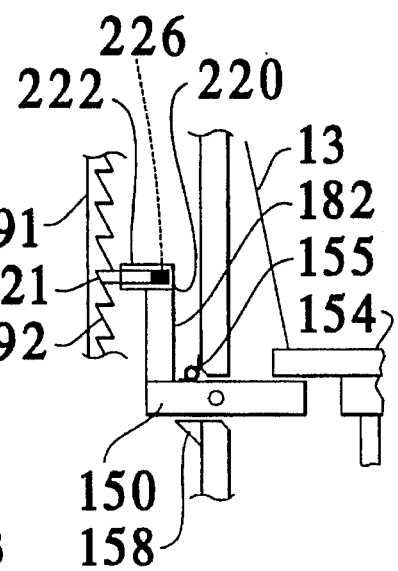
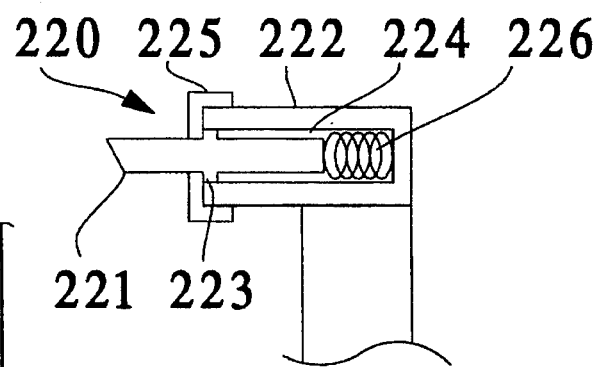
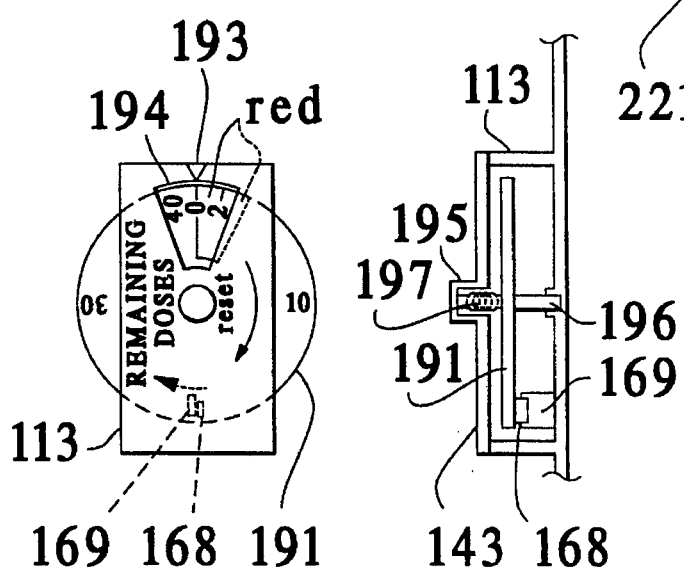
Fig. 11A  Fig. 11B  Fig. 11C  Fig. 11D  Fig. 11E

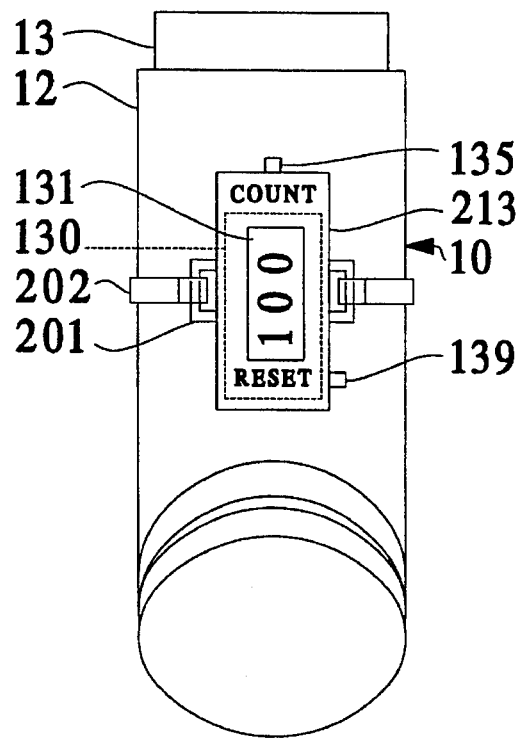
Fig. 12A
Fig. 12B
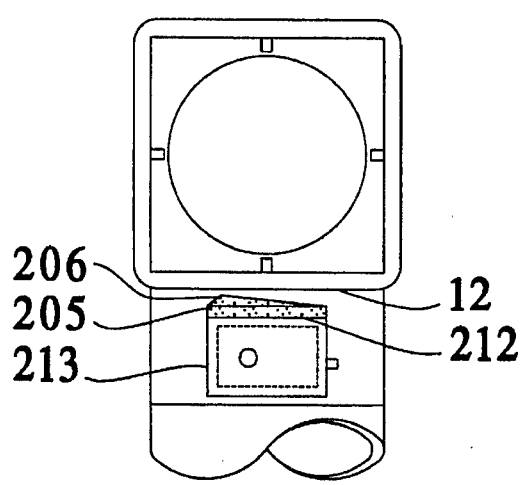
Fig. 12C
Fig. 12D

PRESSURIZED AND METERED MEDICATION DOSE COUNTER ON REMOVABLE SLEEVE

BACKGROUND OF THE INVENTION

1. Field of the Invention.

The present invention relates to electronic and mechanical devices for recording doses of pre-measured, aerosol-delivered prescription and over-the-counter medication released from a pressurized canister contained in a patient-held dispensing unit. The invention is used in conjunction with conventional aerosol medication dispensing devices and is also used for the purpose of keeping an accounting of the number of doses dispensed from the pressurized canister. This method of medication delivery is utilized to treat and control asthma and other respiratory diseases afflicting approximately eleven million adults and children.

2. Description of the Related Art

It is of absolute necessity to keep an accurate record of the number of medication doses dispensed from a pressurized canister in order not to exceed the number of safe doses indicated by a manufacturer. Exceeding a manufacturer's indicated safe dose rapidly increases the potential for prematurely running out of the actual medication in the canister, and eventually dispensing only the remaining propellant. This unexpected depletion of medication can lead to either an aggravation of the disease symptoms, an increased need for medication, or, in extreme cases, hospitalization to bring the disease under control. Conversely, an overly cautiously approach to the number of the manufacturer's indicated safe doses by prematurely throwing away the canister before the medication is actually used up results in an increase in costs for the patient due to the waste of the remaining safe doses in the medication canister.

There is a general lack of knowledge among patients and health care professionals concerning pressurized medication dispensers and their limitations. Uninformed patients shake the canister and listen to the sound of the liquified gas propellant which may not contain the proper amount of medication in suspension for a prescribed dose. Others spray in the air to observe the mist which may be deficient in medication, while others just guess. Informed patients utilize manual recording of each use and/or calculate the date and time of day when the last fully safe dose is reached.

The latter method is complicated and prone to error, as some medications are used on demand (i.e., before athletic activity or at the onset of disease symptoms). The same or other medications may be utilized as a doctor directs at pre-determined intervals which may change over the life cycle of the pressurized medication canister. Many patients are often on more than one medication delivered at different time intervals which can further complicate the counting process.

Thus, it is a problem in the prior art to provide the patient with an accurate count of the safe doses remaining in a metered and pressurized medication canister.

It is also a problem in the prior art to provide the patient with a visual warning about the impending and final exhaustion of the manufacturer's designated "safe" limit of medication doses contained within a metered and pressurized canister.

SUMMARY OF THE INVENTION

A specific object of the present invention is to provide a device for both the automatic and the manual recording of the dispensing of metered medication from a patient-activated, pressurized canister.

Another object is to give a warning of the pending depletion of "safe" limits of medication in order to provide sufficient time for procurement of a stand-by replacement canister in advance of final exhaustion.

Yet another object is to provide a warning upon reaching the maximum number of "safe" doses of medication and also to provide a warning about the need for immediate canister replacement.

Yet another object is to provide for a counting device which will not interfere with, nor hinder, the dispensing of medication.

Still another object is to maintain current manufacturers' use of identifying color codes, dispenser body dimensions, and canister sizes.

Still another object of this invention is to provide counter recording embodiments which are simple in construction, which are inexpensive to manufacture, and which use either conventional digital electronics or mechanical wheel counters in common use today.

The foregoing objects and other advantages are achieved through the use of several counting systems to activate either electronic or mechanical count-down devices.

Each counting system includes a counter in a container that either is constructed as an integral part of a colored or a clear plastic sleeve, which is then slipped over the main body of a manufacturer's dispenser, or is constructed as an integral part of a modified manufacturer's dispenser body. Alternatively, the counter is attached either temporarily or permanently either to the main body of the manufacturer's dispenser or to a plastic sleeve that is then slipped over the main body of the dispenser.

Furthermore, each counting system contains either an electronic or a mechanical counting device housed in the container.

In addition, several counting systems contain either an external plunger trigger, or an internal lever trigger built into either the body of the manufacturer's dispenser or the body of a counter sleeve device. This trigger automatically activates the counting device while dispensing each medication dose.

Also, several systems provide for the user to activate the counting device in conjunction with, but independent of, the dispensing of each medication dose.

All counting systems provide advance visual warning of the pending need for medication canister replacement. In addition, electronic-based devices can incorporate auditory warnings.

Mechanical counting devices provide for operational lock-up when the manufacturer's "safe" dose limit is reached. Both electronic and mechanical counting devices can provide for resetting the counter device when the counter systems are utilized in conjunction with either reusable sleeve devices or reusable manufacturer's dispensers. Furthermore, the electronic and the mechanical counting devices can be transferred and attached to the manufacturer's replacement dispensers.

The foregoing objects, together with other objects, features and advantages of the invention will be more apparent upon referring to the following specifications and drawings.

BRIEF DESCRIPTION OF THE DRAWINGS

FIG. 1A is a side elevational view of a prior art device;

FIG. 1B is a partially broken away top plan view of the prior art device;

FIG. 1C shows the use of the prior art device in operation;

FIG. 2B is an enlarged front elevational view of a plunger trigger device used in the sleeve device of the first embodiment;

FIG. 3A is a top plan view of a second embodiment;

FIG. 3B is a side elevational view of the second embodiment;

FIG. 3C is a top plan view of a third embodiment;

FIG. 3D is a side elevational view of the third embodiment;

FIG. 5A is a schematic illustration of a first embodiment of an electronic circuit used in the present invention;

FIG. 5B is a table relating preset amounts of medication doses available, whether or not a jumper in the electronic circuit is in place;

FIG. 5C is a schematic illustration of a second embodiment of the electronic circuit used in the present invention;

FIG. 6A is a partially broken away side elevational view of a fifth embodiment of the present invention;

FIG. 6B is an enlarged side elevational view of a lever-type trigger device used in the fifth embodiment;

FIG. 6C is a front elevational view of the fifth embodiment;

FIG. 7A is a front elevational view of a sixth embodiment with a cover in place;

FIG. 7B is the front elevational view of the sixth embodiment with the cover removed;

FIG. 7C is a partially broken away side elevational view of the sixth embodiment;

FIG. 7D is an enlarged side view of details shown in FIG. 7C;

FIG. 7E is an enlarged top plan view of one detail shown in 7D;

FIG. 7F is an enlarged top plan view of another detail shown in FIG. 7D;

FIG. 7G is a partial front elevational view of a seventh embodiment having a reset feature;

FIG. 7H is a partially broken away side elevational view of details shown in FIG. 7G;

FIG. 8A is a front elevational view of an eighth embodiment with cover in place;

FIG. 8B is the front elevational view of the eighth embodiment with both the cover and the counter wheels removed;

FIG. 8C is a partially broken away and enlarged side elevational view of the eighth embodiment;

FIG. 8D is the front elevational view of the eighth embodiment with only the cover removed;

FIG. 8E is a partial front elevational view of the eighth embodiment having a reset feature;

FIG. 8F is a side elevational view of details shown in FIG. 8E;

FIG. 9A is a front elevational view of a ninth embodiment with cover in place;

FIG. 9B is the front elevational view of the ninth embodiment with the cover removed;

FIG. 9C is a partial front elevational view of a modified ninth embodiment having a reset feature;

FIG. 9D is a side elevational view of details shown in FIG. 9C;

FIG. 10A is a front elevational view of a tenth embodiment;

FIG. 10B is a partially broken away and enlarged side elevational view of the tenth embodiment;

FIG. 10C is an enlarged view of details shown in FIG. 10B;

FIG. 10D is a partial front elevational view of a modified tenth embodiment having a reset feature;

FIG. 10E is a side elevational view of details shown in FIG. 10D;

FIG. 11A is a front elevational view of an eleventh embodiment;

FIG. 11B is a partially broken away and enlarged side elevational view of the eleventh embodiment;

FIG. 11C is an enlarged view of details shown in FIG. 11B;

FIG. 11D is a partial front elevational view of a modified eleventh embodiment having a reset feature;

FIG. 11E is a side elevational view of details shown in FIG. 11D;

FIG. 12A is a front elevational view of a twelfth embodiment showing a first method of attaching the counter housing to the dispenser body;

FIG. 12B is a top plan view of the twelfth embodiment also showing the first method of attaching the counter housing to the dispenser body;

FIG. 12C is an enlarged top plan view of the twelfth embodiment showing a second method of attaching the counter housing to the dispenser body;

FIG. 12D is an enlarged top plan view of the twelfth embodiment showing a third method of attaching the counter housing to the dispenser body;

DETAILED DESCRIPTION OF THE PREFERRED EMBODIMENTS

Figure 2C:
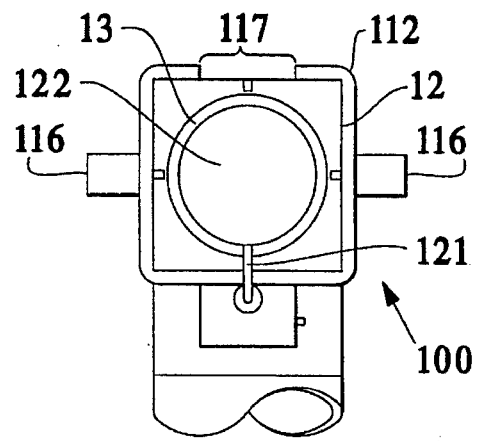
FIG. 2C is a partially broken away top plan view of the first embodiment.

FIGS. 1A–1C are offered to provide a background as to the construction and operation of a current manufacturer's metered dose dispenser system 10. FIGS. 1A and 1B show a representative prior art device upon which the present invention is an improvement while FIG. 1C depicts the mode of operating the prior art device.

FIG. 1A depicts a side elevational view of the complete manufacturer's metered dose dispenser system 10. This prior art device has a uniquely colored plastic dispenser body 12 with an integral offset mouthpiece 15, a pressurized metal canister 13 containing a liquified gas propellant mixed with medication, and a separate contrasting color plastic dust cap 14. The medication canister 13 is installed within the dispenser body 12, base up. A medication transfer tube 16 is partially inserted, with a snug fit, into an orifice box 17 and is restrained from downward movement by an internal stop 19. When sufficient finger pressure is applied by a user to the concave base of the medication canister 13, the canister 13 moves downward as the medication transfer tube 16 recedes into the body of the canister 13. This downward action allows the release of a pre-measured volume of propellant and suspended medication which travels down the medication transfer tube 16, through the orifice box 17, and discharges as a vapor through the offset mouthpiece 15. The medication canister 13 automatically returns to its starting position when the downward finger pressure is released.

FIG. 1B depicts a top plan view of the square-shaped dispenser body 12 favored by a particular prior art manufacturer. Other manufacturers favor modified squares, ellipses, or other dimensional variations, plus color variances for tactile and visual recognition. The dispenser body 12 contains guide channels 18 to provide for lateral stability and for ease of installation of the medication canister 13.

FIG. 1C depicts the operating position of the prior art device utilized by a patient to deliver medication. In sequence, the patient shakes the manufacturer's dispenser system 10 to place the medication contained within the canister 13 into suspension. The dispenser body 12 is then held in the hand with the forefinger positioned on the base of the medication canister 13. A deep exhale is performed and the offset mouthpiece 15 is placed in the mouth, tightly sealed by the lips. The base of the medication canister 13 is pressed downward by the user's forefinger at the start of a deep inhale, thereby allowing a metered amount of vaporized medication to enter the offset mouthpiece 15 and to be ingested into bronchi and lungs. When the finger pressure is released, the medication canister 13 returns to the starting position and the sequence is completed. Required daily or periodic maintenance involves the steps of removing the medication canister 13, rinsing the dispenser body 12 and orifice box 17 (not shown in FIG. 1C) so that there is no medication build-up, air drying the dispenser body 12 and the orifice box 17 (not shown in FIG. 1C), and finally placing the medication canister 13 back into the dispenser body 12.

FIGS. 2A–2D depict a first embodiment intended for the automatic recording of the dispensing of pressurized and metered medication doses. This first embodiment includes a slip-on counter sleeve body 112 containing a plunger-type trigger device 120, an electronic counter device 130, and other features collectively designated as a counter sleeve device 100.

Figure 2D:
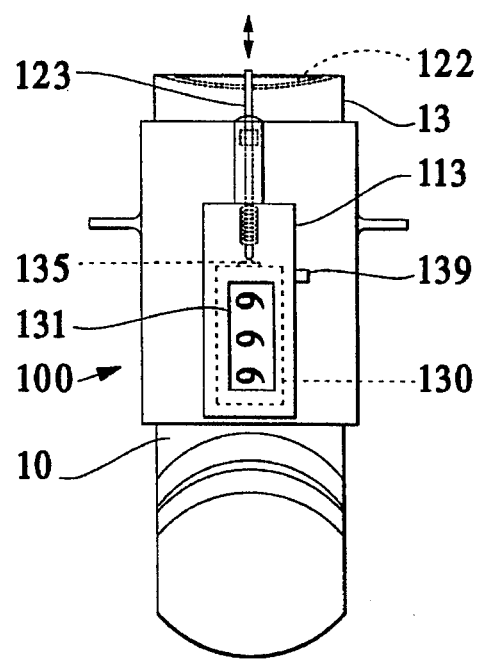
FIG. 2D is a front elevational view of the first embodiment.
Figure 2A:
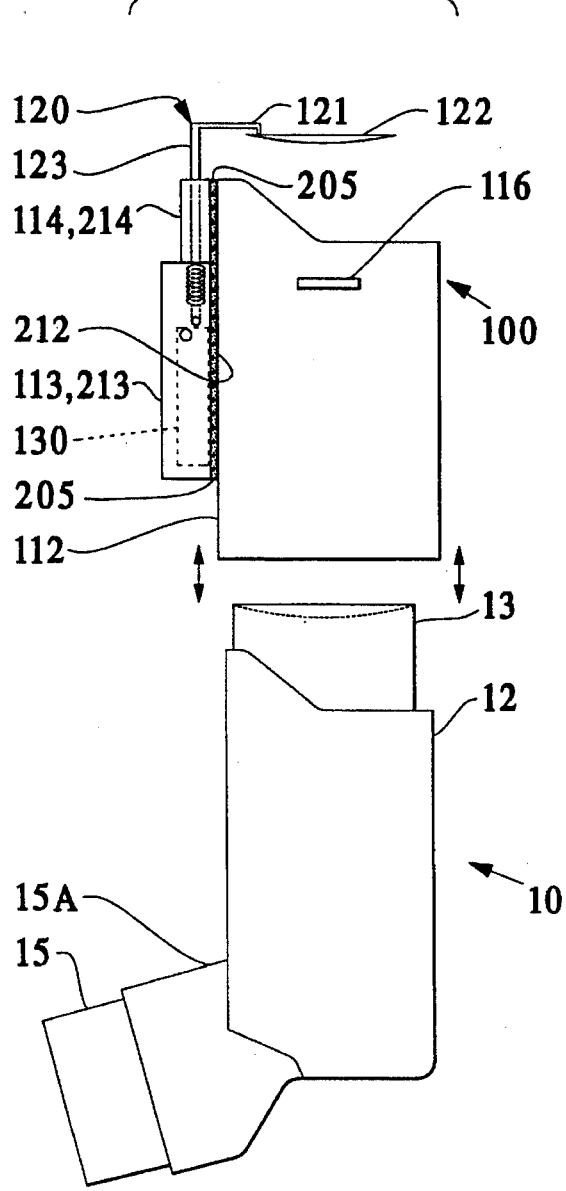
FIG. 2A is an exploded side elevational view of a sleeve device which is a part of a first embodiment of the present invention that is slipped over the prior art device shown in FIGS. 1A, 1B and 1C.

FIG. 2A depicts an exploded side elevational view of the counter sleeve device 100 above the manufacturer's dispenser system 10 over which it is to be slipped and installed. The counter sleeve device 100 has a counter sleeve body 112 which is constructed of either a matching colored or a clear plastic material. The counter sleeve body 112 conforms to fit over the cross-sectional and vertical dimensions of the dispenser body 12. A support column 114 for an external plunger-type trigger device 120 and a counter housing 113 for an electronic counter device 130 are constructed on one exterior wall of the counter sleeve body 112. A horizontal connector 121 of the plunger-type trigger device 120 is attached to a concave disk 122 which has a slightly smaller diameter than the concave base of the medication canister 13. A rounded vertical trigger shaft 123 of the plunger-type trigger device 120 extends vertically downward through the support column 114 and into the interior of the counter housing 113.

Installation is accomplished, as shown in FIG. 2A, by sliding the counter sleeve device 100 downwardly over the dispenser body 12 until the counter sleeve device 100 firmly rests on a semicircular surface 15A formed at a juncture of the dispenser body 12 and the offset mouthpiece 15. Two side projections 116 provide aid as finger grips for installation and removal of the counter sleeve device 100 from the dispenser body 12.

Alternatively, as shown only in FIG. 2A, an independently constructed support column 214 containing the plunger trigger device 120 and a connected counter housing 213 may be permanently attached by a manufacturer to the counter sleeve body 112 utilizing a contact-type adhesive 205 applied to the contoured rear wall 212 in a manner depicted in FIG. 12C.

Returning to FIG. 2A, the combined unit of the counter housing 213 and the support column 214 is then pressed against the counter sleeve body 112 at a designated location to effect a permanent installation.

The aforementioned alternative method of attachment of the independently constructed support column 214 and the counter housing 213 connected thereto may likewise be utilized in the forthcoming embodiments shown in FIGS. 3, 4, 8, 9 and 10, wherein the combined unit of the counter housing 213 and the support column 214 may be permanently attached with a contact-type adhesive 205 by a manufacturer either to the counter sleeve body 112 or directly onto the manufacturer's dispenser body 12.

This alternate construction and attachment method is applicable for use on all counter sleeve devices 100 and manufacturer's dispenser systems 10 wherein the external plunger trigger device 120 is utilized. A benefit of this embodiment is the elimination of the need for a manufacturer to retool in order to produce a modified dispenser body 12.

FIG. 2B depicts an enlarged front elevational view of the plunger-type trigger device 120 and also shows the construction of the rounded vertical trigger shaft 123 and the support column 114. The vertical trigger shaft 123 enters the support column 114 through a water-tight seal 124 and proceeds downwardly through a turning chamber 125, then through key slots 126, ending within the counter housing 113. Two key projections 127 extend within the key slots 126 to provide support for the vertical trigger shaft 123 during normal operations. A compression spring 128 is attached near the base of the vertical trigger shaft 123 and rests against the top interior wall of the counter housing 113. For either removal or replacement of the medication canister 13 (not shown in FIG. 2B), the vertical trigger shaft 123 is lifted against the compression spring 128, thereby raising the key projections 127 into the turning chamber 125 and clearing the key slots 126. The vertical trigger shaft 123 is then turned 90 degrees, thus allowing the concave disk 122 to clear the concave bottom of the medication canister 13 (not shown in FIG. 2B). The release of the lifting pressure on the vertical trigger shaft 123 allows the key projections 127 to rest on the lower floor of the turning chamber 125, thereby resulting in a lock-out of the plunger-type trigger device 120 so that inadvertent operation of an electronic dose count microswitch 135, shown in FIG. 2D, is prevented when the medication canister 13 is either removed for maintenance or replaced.

FIG. 2C depicts a top plan view of the counter sleeve device 100 shown in the top part of FIG. 2A and installed on a manufacturer's dispenser system 10 shown in a lower half of FIG. 2A. Returning to FIG. 2C, the counter sleeve body 112 is constructed with a slightly narrower inside rear dimension and also with a vertical break opening 117 in a rear wall of the counter sleeve body 112. The opening 117 widens slightly when the counter sleeve device 100 is installed downwardly over the dispenser body 12. The natural tendency of the plastic material of the counter sleeve body 112 to return to its original shape results in creating the friction necessary to hold the counter sleeve device 100 in place on the dispenser body 12. The concave disk 122, which is attached to the horizontal connector 121, is centered over and seated on the concave base of the pressurized medication canister 13. The two side projections 116 provide aid to the user for installation and removal of the counter sleeve device 100 from the dispenser body 12.

FIG. 2D depicts a front elevational view of the counter sleeve device 100 installed on the manufacturer's dispenser system 10 shown in the lower half of FIG. 2A. Returning to FIG. 2D, the counter housing 113 includes the electronic counter device 130 having a visible three-digit liquid crystal counter display 131, a power supply (not shown), and the pressure-responsive electronic dose count microswitch 135 to activate a preprogrammed microcontroller to be discussed later in regard to FIGS. 5A and 5C. The electronic counter device 130 records each delivery of a medication dose. The user applies a downward pressure on the base of the pressurized medication canister 13 and on the concave disk 122, thus causing the lower end tip of the vertical trigger shaft 123 to move downwardly. Upon contact, the tip closes the electronic dose count microswitch 135 located within the counter housing 113. The dose count microswitch 135 activates the electronic counter device 130, thus causing a number on the LCD counter display 131 to be reduced by a count of one so that a visual status signal is sent to the patient. The electronic dose count microswitch 135 returns to the open position when the patient releases the downward finger pressure on the medication canister 13 and the concave disk 122, thereby allowing the vertical trigger shaft 123 to move upwardly due to the lifting force provided by the medication canister 13 returning to its normal rest position. An external pressure-sensitive count reset switch 139 is installed in a side wall of the counter housing 113 in order to reset the LCD counter display 131 in all embodiments where the electronic counter device 130 is intended for reuse. The function and the operation of the count reset switch 139 are described later with reference to FIG. 5C.

FIGS. 3A–3D depict second and third embodiments which further show the versatility of the counter sleeve device 100 for utilization on a variety of manufacturers' dispenser systems 10. Alternate mounting locations for the plunger-type trigger device 120, the counter sleeve device 100, the support column 114, and the counter housing 113 may be preferred for operating the invention.

For example, FIGS. 3A and 3B depict a manufacturer's preference for a somewhat elliptical dispenser body 12. In this second embodiment, the counter sleeve device 100 of the invention is constructed of either clear or matching color plastic and conforms to the dimensions of the manufacturer's elliptical dispenser body 12, thereby maintaining easy tactile and visual identification for users. The rear mounting of the plunger-type trigger device 120, the support column 114, and the counter housing 113 is an illustrative second embodiment.

FIGS. 3C and 3D illustrate the third embodiment in top plan and side elevational views, respectively, of another manufacturer's modified, rectangular-shaped, dispenser body 12. The counter sleeve device 100 is manufactured of either clear or matching color plastic material and conforms closely to the dimensions of the manufacturer's rectangular-shaped, dispenser body 12. The side mounting of the counter housing 113, the plunger-type trigger device 120, and the support column 114 is an illustrative third embodiment.

Figure 4A:
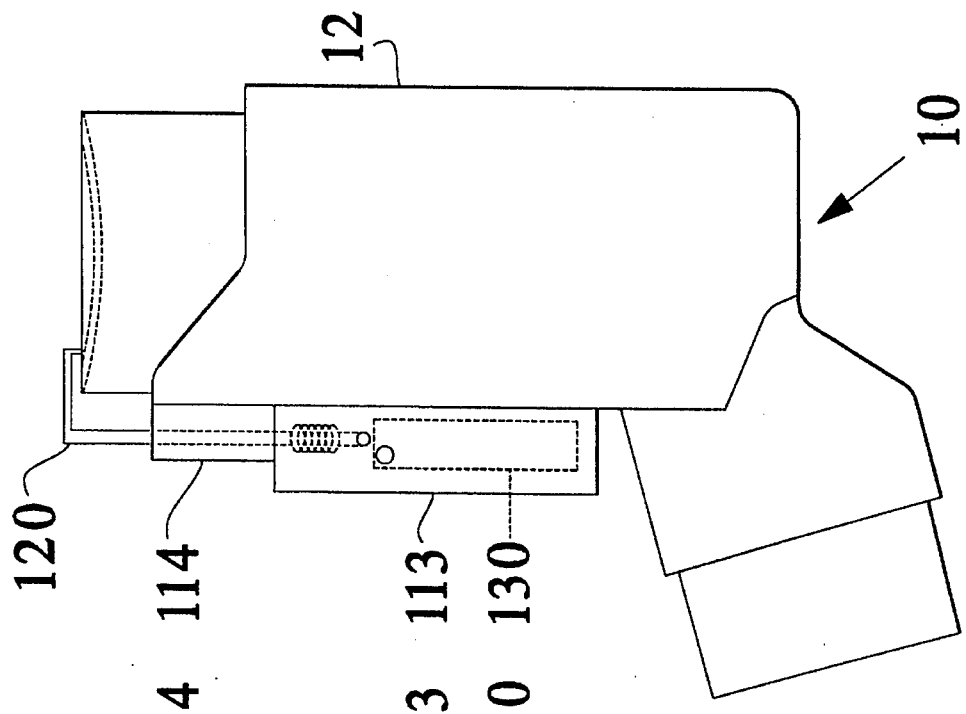
FIG. 4A is a partially broken away top plan view of a fourth embodiment.
Figure 4B:
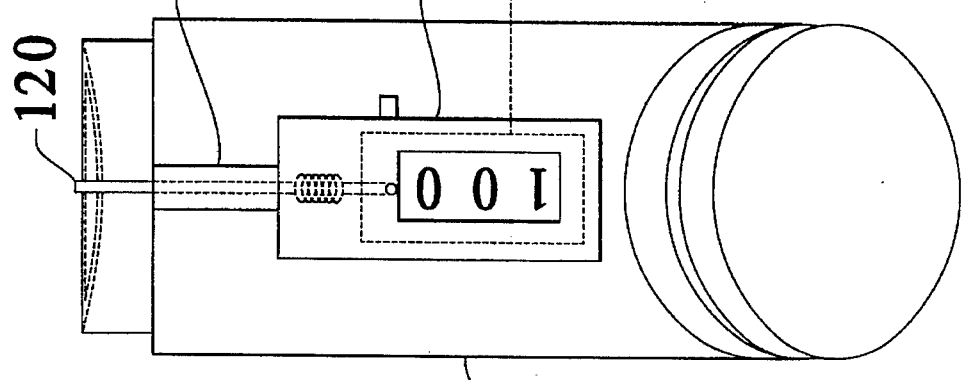
FIG. 4B is a front elevational view of the fourth embodiment.
Figure 4C:
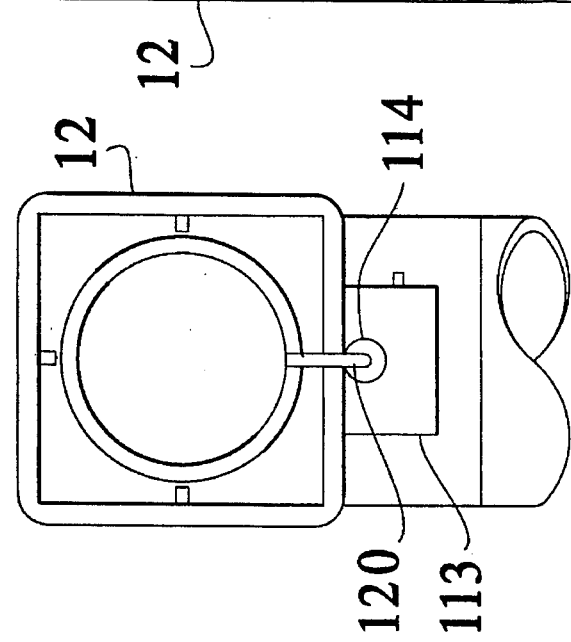
FIG. 4C is a side elevational view of the fourth embodiment.

FIGS. 4A–4C depict top plan, front, and side elevational views, respectively, of a plunger-type trigger device 120 installed directly on a manufacturer's modified dispenser system 10 which includes the support column 114 and an electronic counting device 130 installed within the counter housing 113 that is constructed as an integral part of the dispenser body 12 by the manufacturer.

Alternatively, as shown in FIG. 2A only, the independently constructed counter housing 213 and the support column 214 may be directly attached to the dispenser body 12 with the contact-type adhesive 205. Returning to FIGS. 4A–4C, all features and operations of this fourth embodiment are otherwise the same as described in reference to the first embodiment shown in FIGS. 2A–2D. The modifications and attachments may be located on either the front, the sides, or the back of the dispenser body 12, as described in regard to the second and third embodiments shown in FIGS. 3A–3D.

FIG. 5A is a schematic drawing of a first embodiment of the electronic counter device 130. FIG. 5C is a schematic drawing of a second embodiment of the electronic counter device 130. FIG. 5B is a table correlating electrical jumper installation to preset the starting count of safe medication doses available to a patient. The construction of the electronic counter device 130 was initially shown generally in FIG. 2D and again in FIG. 4B. The electronic counter device 130, once activated by a trigger device (not shown in FIGS. 5A and 5C), informs a user as to the number of safe doses of medication remaining in the pressurized medication canister 13 of FIGS. 2A, 2C, 2D, 4B, and 4C. This same electronic counter device 130 will also be seen later in the embodiments shown in FIGS. 6A, 6C, and 12A.

In FIG. 5A, an FE2201 3 ½ digit liquid crystal display (LCD) made by the AND Corp. is preferred for the LCD counter display 131. Either an Oki MSM5054 or a Sanyo LC5730 may serve as a microcontroller 132 that possesses a self-contained preprogrammed memory and display drivers. The microcontroller 132 also features a program halt state to reduce power consumption when the counter device 130 is not active. Either an Eveready ER803BP 1.5-volt lithium battery or an equivalent NEDA 5007C standard battery is a preferred power source 133. A positive terminal for the power source 133 is connected through a battery circuit $V_{DD}$ to a terminal of the normally open dose count microswitch 135 and to a predisposed pin VDD on the microcontroller 132. A negative terminal for the power source 133 is connected to a predisposed pin VSS1 located on the microcontroller 132. Two ERIE Z5V-0.1MFD capacitors 134 are connected to the power source 133 and predisposed pins VEE and VSS2 which are needed to raise the power level required to operate the LCD counter display 131. An Epson American MC405 32.768 KHZ crystal oscillator 137, installed on predisposed pins XT and $\overline{XT}$, acts as an internal clock to control the timing of the microcontroller 132 program functions. An ITW 60–1000 pressure-sensitive unit may serve as the dose count microswitch 135, initially seen in FIG. 2A, and is connected between the battery circuit $V_{DD}$ and a predisposed pin S1. Closure of the dose count microswitch 135 activates the microcontroller 132.

Continuing with FIG. 5A, two predisposed pins S3 and S4 are available on the microcontroller 132 to which electrical jumper connections J1 and J2, collectively identified as jumper 136, may or may not be installed to connect with the battery circuit $V_{DD}$. The status of the jumper 136 determines the starting count on the LCD counter display 131. The microcontroller 132 is capable of being programmed to contain up to four starting counts ranging from "0" to "999", thereby allowing one electronic counter device 130 to be utilized on a number of counter sleeve devices 100 and manufacturers' dispenser systems 10.

The Jumper Installation Table of FIG. 5B depicts four representative starting medication dose counts of "100", "118", "150" and "200" indicated in the table column labeled Program Preset. The next two columns, labeled Jumpers J1 and J2, indicate the presence or absence of a jumper connector by utilizing the symbol "0" to indicate that no jumper 136 is installed and an "X" to denote that one jumper 136 is installed. As an example, a jumper 136 installed at J1 in FIG. 5A will result in only a signal at the pin S3 located on the microcontroller 132. Referring to the Table in FIG. 5B, this example will cause the program of the microcontroller 132 to set an initial starting count in the LCD counter display 131 of "118".

The following operational sequence of the electronic counter device 130 of FIG. 5A is based on a manufacturer's safe medication dose limit of "100". No jumper 136 is installed at J1 or J2 according to the Table in FIG. 5B. The power source 133 is inserted into the electronic counter device 130, thus energizing the microcontroller 132 and the circuit for the LCD counter display 131. The program of the microcontroller 132 queries the status of the jumpers 136 and, after receiving no electrical signal at either pin S3 or pin S4, sends a signal through the display drivers to indicate an initial count of "100" on the LCD counter display 131. Thereafter, the microcontroller 132 deactivates itself by its own program while the LCD counter display 131, connected to a separate circuit, remains operational and continues to display a reading of "100".

When a user depresses the concave disk 122, best shown in FIG. 2D, with the finger to dispense the first medicine dose, the tip of the vertical trigger shaft 123 seen in FIG. 2D moves downwardly and closes the dose count microswitch 135. When the user releases the concave disk 122 by removing the finger, the lifting pressure of the medication canister 13 returning to its starting position forces the vertical trigger shaft 123 upwards, thus allowing the dose count microswitch 135 to open after the medication is dispensed. As seen in FIG. 5A, this action causes an electrical signal to flow from the power source 133, through the circuit $V_{DD}$, then through the dose count microswitch 135, and into the microcontroller 132 at the pin S1. The signal reactivates the microcontroller 132 which, following pre-programmed steps, sends another signal through the display drivers to reduce the count on the LCD counter display 131 by "1". The display now indicates that there are "099" remaining safe doses of medication. The microcontroller 132 again deactivates itself by its own program while the LCD counter display 131 remains active and continues to display "099".

This cycle is repeated for each medication dose delivered until the count of "010" remaining safe doses is indicated on the LCD counter display 131. With the next medication dose, the LCD counter display 131 reduces one additional unit to "009". At this point, the program of the microcontroller 132 directs the LCD counter display 131 to turn off and on three times, thus providing a visual warning of the pending loss of a safe level of medication. The microcontroller 132 again deactivates itself by its own program. This sequence continues to occur for each subsequent dose application until the LCD counter display 131 reads "001". The next and final safe medication dose application results in the LCD counter display 131 decreasing to "000". The program in the microcontroller 132 now directs the LCD counter display 131 to turn off and on a selected number of times, e.g. ten times, thus ending with "000" on permanent display. The microcontroller 132 deactivates completely by its own program and further closure of the dose count microswitch 135 is not acknowledged.

The preceding discussion describes a basic disposable electronic counter device 130 primarily intended for use on a manufacturer's dispenser system 10 wherein the manufacturer does not offer a separate replacement medication canister 13.

FIG. 5C depicts a second embodiment of the electronic counter device 130 shown in FIG. 5A. This second embodiment in FIG. 5C has two elements not found in the first embodiment of FIG. 5A. The first additional element is a buzzer alarm 138 intended as an audible safety warning feature. The buzzer alarm 138 is an Erie model DK1M22EPP-4001 buzzer connected to a predisposed pin BD and to the power source 133 through the circuit $V_{DD}$. For each closure of the dose count microswitch 135, the program in the microcontroller 132 directs a signal through an internal buzzer driver, thus causing the buzzer alarm 138 to issue a short audible sound in conjunction with corresponding changes in the count shown on the LCD counter display 131. For example, if the resulting display count is "099" to "010", one alarm is sounded; if the resulting display count is "009" to "001", three alarms; and finally on reaching "000", ten alarms. This buzzer alarm 138 may also be added either to the previously described first embodiment of the electronic circuit depicted in FIG. 5A or to the second embodiment of the electronic circuit depicted in FIG. 5C.

Returning to FIG. 5C, the second element added to the second embodiment and not found in the first embodiment of FIG. 5A is an ITW 60–1000 pressure-sensitive count reset switch 139 connected to the predisposed pin S2 located on the microcontroller 132 and linked to the power source 133 through the circuit $V_{DD}$. The count reset switch 139 is mounted through a watertight, sealed opening in a side wall of the counter housing 113, as best shown in FIG. 2D. After the LCD counter display 131 counts down to "000" in FIG. 5C, the user depresses the count reset switch 139 with the finger, thus allowing a signal from the circuit $V_{DD}$ to enter the microcontroller 132 through the pin S2. The signal reactivates the microcontroller 132. The program then queries the status of the jumpers 136, and, if sensing no signal at either pin S3 or pin S4, sends a signal through the internal display drivers to reset the LCD counter display 131 to the initial starting count of "100". This count reset switch 139 is utilized for all embodiments in which either the counter sleeve device 100 of FIG. 2A or the manufacturer's dispenser system 10 of FIG. 4C and forthcoming FIGS. 6A and 12A are intended for reuse.

FIGS. 6A–6C introduce a fifth embodiment of the invention in which an internal lever-type trigger device 150 is utilized to activate the electronic counter device 130. FIG. 6A is a cutaway side elevational view of a manufacturer's modified dispenser system 10 and a pressurized medication canister 13. A first modification of the dispenser body 12 is that the counter housing 113 is manufactured as a part of an outside wall of the dispenser body 12 housing the electronic counter device 130 shown in FIGS. 5A and 5C. A second modification of the dispenser body 12 is that the lever-type trigger device 150 is intended to activate the electronic counter device 130 and is further detailed in FIG. 6B. The lever-type trigger device 150 extends from within the dispenser body 12, through a flexible watertight seal 151, and terminates within the counter housing 113. A fulcrum of the lever-type trigger device 150 includes two fulcrum pins 152 inserted into two receivers 157 contained within the outside wall of the dispenser body 12. As shown in FIG. 6A, the top of the internal leg of the lever-type trigger device 150 rests against the bottom of a sealing ring 154 on the medication canister 13 and is held in contact by downward pressure exerted by a coil-type spring 155 shown only in FIG. 6B. A lever trigger stop 158 prevents excessive downward movement of the external section of the lever-type trigger device 150 when the medication canister 13 is removed for either maintenance or replacement. The dose count microswitch 135 is fixed within the counter housing 113, with the pressure switch side down, at a set distance above the end of the external section of the lever-type trigger device 150.

Returning to FIG. 6A and referring to FIG. 6C, the operational sequence for the patient is as follows. Initially, the patient uses a finger to depress a base of the medication canister 13, thus resulting in a downward movement of an internal section of the lever-type trigger device 150. This action results in a corresponding upward movement of the other end, i.e. the external section of the lever-type trigger device 150. The lever-type trigger device 150 then pivots in a see-saw motion around the fulcrum pins 152, thereby engaging and effecting closure of the dose count microswitch 135, thus resulting in a reduction in the count on the LCD counter display 131 in FIG. 6C by one. Returning to FIGS. 6A and 6B, upon release of the finger pressure applied by the user, the medication canister 13 rises to its normal rest position. The coil spring 155 applies downward pressure on the external leg of the lever-type trigger device 150, thereby opening the dose count microswitch 135 while continuing contact is maintained between the internal leg of the lever-type trigger device 150 and the underside of the sealing ring 154 on the medication canister 13. The lever-type trigger device 150 is then returned to its initial position to record the next medication dose.

Returning to FIG. 6C, the patient continues the previous operational sequence for 99 additional medication doses at which time the LCD counter display 131, as shown in FIG. 5A, indicates a permanent display of "000" safe doses remaining in the medication canister 13.

Returning to FIG. 6C, if the dispenser system 10 is of the disposable type, it is discarded along with the attached electronic counter device 130. If the dispenser system 10 is intended for reuse with a replacement medication canister 13, then the count reset switch 139 is provided to reset the LCD counter display 131 to the original starting count of "100", as shown in FIG. 5C, and the operational sequence is repeated.

FIGS. 7A–7D introduce a sixth embodiment having a three-wheeled mechanical counter installed within a counter housing 113 constructed as an integral part of the manufacturer's dispenser body 12 and activated by the internal lever-type trigger device 150. In a modified sixth embodiment, a counter reset is depicted for use when the manufacturer's dispenser system 10 is intended for reuse.

FIG. 7A presents a front elevational view of an assembled unit consisting of the counter housing 113 mounted on a front face of the manufacturer's dispenser body 12. A cover 143 contains three portals 160A, 160B and 160C, each exposing a numeric digit representing units, tens and hundreds, respectively, when read from bottom to top. When combined, the resulting number indicates the number of "safe" medication doses, i.e. "100", remaining in the representative medication canister 13.

FIG. 7B presents a front elevational view of the counter housing 113 with the cover 143, indicated in FIG. 7A, being removed. Of the three counter wheels, there are the following: a units, or driver counter wheel 161; a tens, or first slave counter wheel 162; and a hundreds or second slave counter wheel 163. The following discussion describes the interaction of the three counter wheels and is based on a starting safe medication dose of "100", as displayed in the portals 160 in FIG. 7A. The movement of the lever-type trigger device 150, which causes the clockwise movement of the units driver counter wheel 161, is described in detail in regard to FIGS. 7C–7F which follow.

Continuing with FIG. 7B and referring to the portals 160 in FIG. 7A, when the first dose of medication is delivered, the units driver counter wheel 161 is moved one-tenth of a turn clockwise, thus exposing the digit "9" in the units portal 160A. Simultaneously, a dog 164, attached on the circumference of the units driver counter wheel 161, engages one of ten evenly spaced gear teeth 165 located on the circumference of the tens counter wheel 162, thereby causing the tens counter wheel 162 to revolve one-tenth of a turn counterclockwise and exposing the digit "9" in the tens portal 160B. Simultaneously, the partial revolution of the tens counter wheel 162 drives a dog 166, located on its circumference, to engage one of the ten evenly spaced gear teeth 167 attached on the circumference of the hundreds counter wheel 163, thereby turning the hundreds counter wheel 163 one-tenth of a turn clockwise and exposing the digit "0" in the hundreds portal 160C. The clockwise movement of the hundreds counter wheel 163 also drives a counter wheel stop projection 168, located on the reverse side of the hundreds counter wheel 163, to contact an overlapping body stop projection 169 extending upwardly from the floor 144 of the counter housing 113. The contact between the two stop projections 168 and 169 restrains further clockwise movement of the hundreds counter wheel 163. At this point, the portals 160 exhibit "099" remaining "safe" doses in the medication canister 13. After 99 additional medication doses and 99 additional partial movements of the units driver counter wheel 161, the digit "0" returns to its original starting position in the units portal 160A. Likewise, the tens counter wheel 162, having completed one full revolution, returns to its starting position, and also displays the digit "0" in the tens portal 160B. The hundreds counter wheel 163, not having moved, continues to display the digit "0" in the hundreds portal 160C. The hundreds counter wheel 163 is still constrained from further clockwise movement due to the contact between the two stop projections 168 and 169. The portals 160 now exhibit "000" remaining safe doses.

Continuing with FIG. 7B, an attempted 101st dose, after the manufacturer's safe dose limit of 100 has been reached, results in the dog 164 on the units driver counter wheel 161 engaging a gear 165 on the tens counter wheel 162, and attempting to move the gear 165 counterclockwise. Simultaneously, the dog 166 on the tens counter wheel 162 engages a gear 167 on the hundreds counter wheel 163 and attempts to move the gear 167 clockwise. However, the hundreds counter wheel 163 is constrained from further clockwise movement due to the contact between the two stop projections 168 and 169, thereby prohibiting further movement of all three counter wheels 161, 162, and 163. This condition may be identified as "counter lock-up".

FIG. 7C, in conjunction with FIGS. 7D, 7E, and 7F, depicts the construction and operation of the lever-type trigger device 150 and an attached dog-type drive head device 180 which rotates the units driver counter wheel 161 clockwise so that the dispensing of each dose of medication is recorded.

It may be noted here that a pin-type drive head device 220 shown in forthcoming FIGS. 11B and 11C may be interchanged with the dog-type drive head device 180 shown in FIGS. 7D and 7E.

FIG. 7C depicts a partially cutaway side elevational view of the counter housing 113 which is formed integrally with the outer wall of the manufacturer's dispenser body 12. In FIG. 7C, there are indicated the locations of the following elements already discussed above: the units driver counter wheel 161, the tens counter wheel 162, the hundreds counter wheel 163, the pressurized medication canister 13, the sealing ring 154, the lever-type trigger device 150, the dog-type drive head device 180, the counter wheel stop projection 168, and the body stop projection 169.

The details of the construction and operation of the lever-type trigger device 150 shown in FIG. 7C were discussed previously with regard to the fifth embodiment shown in FIG. 6B. Thus, these details are not discussed again herein. FIG. 7C also depicts the lever-type trigger device 150 passing from the interior of the dispenser body 12 through an opening in the wall of the counter housing 113, thereby allowing for the correct alignment of the dog-type drive head device 180 relative to the gear teeth 185, shown only in FIG. 7F to be located on the back of the units driver counter wheel 161.

The dog-type drive head device 180, depicted in the enlarged side view of FIG. 7D and also in the enlarged top plan view of FIG. 7E, has a triangular dog 181 installed within a partially cut out shaft extension 182 rising vertically from the exterior end of the lever-type trigger device 150. A pin 183 is installed through the body of the shaft extension 182 and passes through a hole located near one corner of the triangular dog 181, thereby allowing upward movement of the horizontal leg of the triangular dog 181 against a spring 184, while downward movement thereof is limited by a vertical leg of the triangular dog 181 contacting a rear wall of the shaft extension 182. At rest, the horizontal leg of the triangular dog 181 lays against one of the ten, evenly spaced gear teeth 185 located on the reverse side of the units driver counter wheel 161 that is also depicted in FIG. 7F.

Returning to FIG. 7D, the downward motion of the medication canister 13 during delivery of the medication dose results in the external leg of the lever-type trigger device 150 moving upwardly, thus causing the triangular dog 181 to contact one of the gear teeth 185 on the units driver counter wheel 161 and thereby turning the units driver counter wheel 161 one position clockwise. At the completion of the delivery of the medication dose, the medication canister 13 rises to its normal rest position, thus allowing the internal leg of the lever-type trigger device 150 also to rise and to maintain contact with the bottom of the sealing ring 154, due to the downward action of the coil-type spring 155. The same spring 155 acts on the external leg of the lever-type trigger device 150 and the attached dog-type drive head device 180 to move them downwardly. The triangular dog 181 then pivots upwardly as the external tip rides down the slope to the next gear tooth 185. The triangular dog 181 then returns to its horizontal starting position as a result of the downward pressure applied by the spring 184 and is ready for the next medication dose to be delivered. The lever trigger stop 158 restrains the downward movement of the external leg of the lever-type trigger device 150 whenever the medication canister 13 is removed for either maintenance or replacement. This restraint prevents the dog-type drive head device 180 from moving downwardly and possibly engaging the wrong gear tooth 185, thus distorting the dose count.

As previously described in regard to FIG. 7B, the three counter wheels 161, 162, and 163 are in a "lock-up" condition after the dispensing of 100 "safe" doses of medication and the reading in the portals 160 in FIG. 7A registers the digits "000". Returning to FIG. 7D, the dog-type drive head device 180 on the exterior end of the lever-type trigger device 150 cannot move upwardly and cannot turn the units driver counter wheel 161 clockwise. Likewise, the opposite or internal end of the lever-type trigger device 150, in contact with the underside of the sealing ring 154, is unable to move downwardly, thereby halting any downward movement of the medication canister 13 that may be caused by pressure applied by a patient during an attempted dose when the medication canister 13 is already depleted of safe medication doses. Thus, the complete counter and dispenser system 10, best seen in FIG. 7A, must be replaced.

FIGS. 7G and 7H jointly depict modifications and operational changes needed to convert the previously described disposable three-wheeled counter into a seventh embodiment having a reusable counter for use when manufacturers offer separate refills of the medication canisters 13 (not shown). The counter housing 113, shown in phantom lines in FIG. 7G, is slightly tapered inwardly near its top end, thus exposing two edges of a slightly enlarged hundreds counter wheel 163. As indicated previously in regard to FIG. 7B, the hundreds counter wheel 163 is incapable of revolving clockwise when the counter wheel stop projection 168 on the underside of the hundreds counter wheel 163 has moved once clockwise and is in contact with the body stop projection 169 which extends upwardly from the floor 144 of the counter housing 113. A counter reset stop projection 170 extends upwardly from the floor 144 of the counter housing 113 and has been added to assist in the reset operations to be discussed. Only two gear teeth 167 are required on the circumference of the hundreds counter wheel 163 in this seventh embodiment. The first gear tooth 167 is required to move the hundreds counter wheel 163 one position clockwise during the first medication dose delivery. The second gear tooth 167 is necessary to effect the counter "lock-up". Another modification in the seventh embodiment is the addition of a hollow cylindrical extension 174 added to the cover 143 of the counter housing 113 in order to receive the shaft 175 of the hundreds counter wheel 163 that projects part way in and rests against a coiled compression spring 173. Resetting the counter requires initially that the patient lift the exposed portions of the hundreds counter wheel 163 with a thumb and an index finger. This action compresses the spring 173 and raises the gear teeth 167 clear of the dog 166 located on the circumference of the tens counter wheel 162.

The hundreds counter wheel 163 is then turned counterclockwise until the counter wheel stop projection 168 contacts the counter reset stop projection 170. The patient then releases the lifting pressure, thus allowing the coiled compression spring 173 to force the hundreds counter wheel 163 and the gear teeth 167 to return to their initial starting positions so that a count of "100" is displayed in the portals 160A, 160B and 160C in FIG. 7A. The three-wheeled counter is now ready to begin the medication dose counting process for a replacement medication canister 13.

FIGS. 8A–8F depict a three-wheeled mechanical counter device activated by the plunger-type trigger device 120, as first shown in FIG. 2A. This eighth embodiment is constructed either as part of the slip-on counter sleeve device 100, as also first seen in FIG. 2A, or as part of either a modified version of or an attachment to the manufacturer's dispenser system 10 of FIG. 4C.

Alternatively, as shown in FIG. 2A only, the independently constructed counter housing 213 and the support column 214 may be attached either to the dispenser system 10 or to the counter sleeve device 100 by the contact-type adhesive 205. Returning to the embodiment shown in FIG. 8A, a three-wheeled counter reset unit is also depicted and can be utilized when either the manufacturer's dispenser system 10 or the counter sleeve device 100 is intended for reuse.

FIG. 8A depicts a front elevational view of the manufacturer's medication dispenser system 10 with the counter housing 113 constructed either as part of a modified version of the manufacturer's dispenser body 12 of FIG. 4C, or as part of the slip-on counter sleeve body 112 of FIG. 2A. The three portals 160A, 160B and 160C in the cover 143 of the counter housing 113 are provided to display hundreds, tens, and units representing the number of "safe" doses remaining in the pressurized medication canister 13. In this eighth embodiment, the number of "safe" doses remaining is indicated as "200". The external portion of the plunger-type trigger device 120, the support column 114, and the medication canister 13 are illustrated at the top of the counter housing 113.

FIG. 8B depicts a front elevational view of the manufacturer's dispenser system 10 or the slip-on counter sleeve device 100 having the attached counter housing 113 with the cover 143 of FIG. 8A and the three counter wheels 161, 162, and 163 of FIG. 8D being removed to expose the basic construction of the plunger-type trigger device 120, the support column 114, and the dog-type drive head device 180.

Moving to FIG. 8C, there is depicted an enlarged side elevational view of the details of the total triggering system that is discussed jointly with FIG. 8B. The plunger-type trigger device 120 includes the concave disk 122 resting in contact with the concave base of the medication canister 13 and being attached to the horizontal connector 121 which in turn is integral with the vertical trigger shaft 123. The vertical trigger shaft 123 proceeds downwardly, entering the support column 114 through the water-tight seal 124, then passing through the turning chamber 125, and emerging from the bottom end of the support column 114 near the bottom third of the counter housing 113. See FIG. 8B. Two key projections 127 are attached to the vertical trigger shaft 123 and rest within the key slots 126 shown in FIG. 8C. These key slots 126 are cut into the walls of the support column 114. The bottom end of the compression spring 128 is attached to the vertical trigger shaft 123 while the upper end of the compression spring 128 rests against the bottom end of the support column 114. The vertical trigger shaft 123 continues downwardly, enters a connecting box 187, and terminates in direct contact with a drive head connector 189. The drive head connector 189 emerges below the bottom of the connecting box 187, and "dog legs" toward the underside of the units driver counter wheel 161 in order to provide proper clearance between the underside of the three counter wheels 161, 162, and 163 of FIG. 8D, the support column 114, and the connecting box 187. This offset arrangement, shown at the bottom of FIG. 8C, also provides proper alignment for the dog-type drive head device 180 connected to the bottom end of the drive head connecter 189. Two key projections 186, necessary to provide lateral stability and to limit upward motion, are attached to the (drive head connector 189 and rest within partial key slots 129 cut into the walls of the connecting box 187. A coil spring 188 is attached at its upper end to the bottom of the connecting box 187 and is attached at its lower end to the drive head connector 189. The construction of the dog-type drive head device 180, attached to the lower end of the drive head connector 189, is fully described with reference to the preceding FIGS. 7D and 7E. For this use, the dog-type drive head device 180 is rotated 180 degrees from top to bottom. It may be noted here that the pin-type drive head device 220 shown in the forthcoming FIGS. 10B and 10C may be interchanged with the dog-type drive head device shown in FIG. 8C.

Continuing with FIG. 8C, the operation of this eighth embodiment has several steps. Initially, the patient depresses the base of the medication canister 13 along with the concave disk 122. This action moves the vertical trigger shaft 123 downwardly within the support shaft 114 and the connecting box 187, wherein the tip of the vertical trigger shaft 123 contacts the upper end of the drive head connector 189. This contact results in the drive head connector 189 moving downwardly, stretching the coil spring 188, and causing the tip of the triangular dog 181 to engage one of the ten gear teeth 185 on the underside of the units driver counter wheel 161. This engagement turns the units driver counter wheel 161 clockwise one position and reduces the units display in the portal 160A of FIG. 8A by one digit. At the completion of the medication delivery, the medication canister 13 and the concave disk 122 rise to their normal rest positions, pulling the vertical trigger shaft 123 upwardly. The drive head connector 189 likewise moves upwardly due to the relaxation of the coil spring 188. The tip of the triangular dog 181 pivots around the pin 183, thus compressing the spring 184 as it rises up the slope to the next gear tooth 185. The triangular dog 181 then returns to a horizontal position behind the following gear tooth 185 due to the pressure exerted by the compressed spring 184. The counting system is now in a position to record the delivery of the next medication dose.

Continuing with FIG. 8C, removal and replacement of the medication canister 13 for routine maintenance will now be described. The process starts with the patient's lifting of the plunger-type trigger device 120 against the compression spring 128 to clear the concave disk 122 above the base of the medication canister 13. At the same time, the two key projections 127, attached to the vertical trigger shaft 123, are lifted into the turning chamber 125 and clear the key slots 126. The concave disk 122 is then rotated 90 degrees horizontally and released, thus allowing the two key projections 127 to rest on the floor of the turning chamber 125, thereby preventing inadvertent movement of the units driver counter wheel 161. The independent drive head connector 189 is not affected by the removal of the medication canister 13 and is held in place by the spring 188 which constrains the drive head connector 189 from upward movement by the two key projections 186 contacting the upper end of the key slots 129. After maintenance is completed and the medication canister 13 is reinstalled, the plunger-type trigger device 120 is lifted and rotated back 90 degrees. When the plunger-type trigger device 120 is released, the concave disk 122 is allowed to rest again in the depression in the base of the medication canister 13. At the same time, the bottom tip of the vertical trigger shaft 123 moves downwardly, due to the stretching of the attached compression spring 128, and resumes contact with the drive head connector 189 in readiness for the delivery of the next medication dose.

FIG. 8D depicts the same three counter wheels 161, 162 and 163 discussed in detail in regard to FIG. 7B. Nevertheless, their interaction is briefly recounted herein, but is based on a manufacturer's safe dose limit of "200", as indicated in the portals 160A, 160B and 160C of FIG. 8A. Returning to FIG. 8D, only two changes, vis-a-vis FIG. 7B, are required to accommodate a count of 200 "safe" doses of medication. The first change is the addition of the digit "2" to the face of the hundreds counter wheel 163. The second change is the relocation of the counter wheel stop projection 168 to a new position located on the underside of the hundreds counter wheel 163. This new position is one position counterclockwise of its position in FIG. 7B to allow for two clockwise movements of the hundreds counter wheel 163 before contacting the counter body stop projection 169 at the completion of the delivery of 200 "safe" doses of medication. Prior to the first medication dose, the units driver counter wheel 161 and the tens counter wheel 162 exhibit the digit "0" in their corresponding portals 160A and 160B of FIG. 8A, while the hundreds counter wheel 163 exhibits the digit "2" in its corresponding portal 160C of FIG. 8A. The combined portals 160A, 160B and 160C signify "200" safe doses of medication available as a starting count.

Referring to FIG. 8C, the first dose of medication results in the triangular dog 181 engaging the gear 185 on the underside of the units driver counter wheel 161, turning the wheel 161 one position clockwise, and exposing the digit "9" in the units portal 160A of FIG. 8A.

Moving to FIG. 8D, one sees that this clockwise movement of the units driver counter wheel 161 simultaneously results in the dog 164, attached on the circumference of the wheel 161, contacting the gear 165 located on the circumference of the tens counter wheel 162. Consequently, the tens counter wheel 162 moves one position counterclockwise and exposes the digit "9" in the tens portal 160B of FIG. 8A.

Returning to FIG. 8D, the movement of the tens counter wheel 162 results in the dog 166, attached on the circumference of the wheel 162, engaging the gear 167 attached on the circumference of the hundreds counter wheel 163 and turning it one position clockwise, thus exposing the digit "1" in the hundreds portal 160C of FIG. 8A. The combined portals 160 of FIG. 8A now indicate "199" doses remaining in the medication canister 13. Returning to FIG. 8D, after the completion of the delivery of 100 doses of medication, the units driver counter wheel 161 will have completed ten revolutions clockwise, returning the digit "0" to its original starting position. The tens counter wheel 162 will have completed one revolution counterclockwise, also returning the digit "0" to its starting position. On the other hand, the hundreds counter wheel 163, having moved only once clockwise during the initial dose delivery, continues to exhibit the digit "1" in the original starting position. The combined portals 160 in FIG. 8A now indicate "100" remaining safe doses in the medication canister 13. Returning to FIG. 8D and also referring to FIG. 8A, the next or 101st medication dose produces the same counter wheel actions as the initial dose described above. Briefly, the units driver counter wheel 161 revolves one position clockwise exhibiting the digit "9" in the units portals 160A, the tens counter wheel 162 revolves one position counterclockwise exhibiting the digit "9" in the tens portal 160B, and the hundreds counter wheel 162 moves, for a second and last time, clockwise one position exhibiting the digit "0" in the units portal 160C. The combined portals 160 now indicate "099" safe doses remaining. At this point, the hundreds counter wheel 163 is restrained from further clockwise movement because the counter wheel stop projection 168 is now in contact with the counter body stop projection 169.

Continuing with FIG. 8D, an attempted 201st medication dose cannot be completed as the total counting device is in "lock up". The hundreds counter wheel 163 cannot move clockwise due to the contact between the two stop projections 168 and 169. As a result, the dog 166 on the tens counter wheel 162 cannot move the hundreds counter wheel 163 clockwise. Likewise, the dog 164 attached to the units driver counter wheel 161 is unable to turn the tens counter wheel 162 counterclockwise.

Moving back to FIG. 8C, the drive head device 180 is unable to move downwardly to turn the units driver counter wheel 161 clockwise, thus resulting in a lack of movement of the drive head connector 189 and the plunger-type trigger device 120, if downward pressure is exerted on the concave disk 122 and the medication canister 13. As a disposable medication dispensing system, the entire unit is now discarded by the patient who commences the use of either the replacement dispenser system 10 or the replacement counter sleeve device 100, shown in FIG. 8A, installed on the replacement dispenser system 10.

FIGS. 8E and 8F jointly depict modifications and operational changes to convert the previously described disposable three-wheeled counter system into a reusable counter for use where manufacturers offer refills of the separate medication canisters 13 (not shown) for use with either the existing dispenser system 10 or the reusable counter sleeve device 100, shown in FIG. 8A, which is intended for transfer to a new dispenser system 10. Returning to FIGS. 8E and 8F, the counter housing 113 is tapered slightly inward at its top, thereby exposing two edges of a slightly enlarged hundreds counter wheel 163. As indicated previously, the hundreds counter wheel 163 is incapable of revolving clockwise when the counter wheel stop projection 168, fixed on the underside of the hundreds counter wheel 163, has moved clockwise twice and into direct contact with the counter body stop projection 169 which extends upwardly from the floor 144 of the counter housing 113. The counter reset stop projection 170, also extending upwardly from the floor 144 of the counter housing 113, has been added to assist in the reset operations to be discussed later. Only three gear teeth 167 are required on the circumference of the hundreds counter wheel 163. The first gear tooth 167 is required to move the hundreds counter wheel 163 one position clockwise during the first delivery of a medication dose, thereby moving the digit "1" into a position previously occupied by the digit "2". The second gear tooth 167 is required to move the digit "0" into the position previously occupied by the digit "1" at the completion of the one hundredth dose of medication. The third gear tooth 167 is necessary to effect the counter "lock-up" described previously. Another modification is the addition of the hollow cylindrical extension 174 to the cover 143 of the counter housing 113 in order to receive the shaft 175 of the hundreds counter wheel 163 that projects part way therein and rests against the coiled compression spring 173.

Continuing with FIGS. 8E and 8F, resetting the counter is accomplished when the patient lifts the exposed portions of the hundreds counter wheel 163 with a thumb and an index finger. This action raises the gear teeth 167 clear of the dog 166 located on the circumference of the tens counter wheel 162. The hundreds counter wheel 163 is then turned counterclockwise until the counter wheel stop projection 168 contacts the counter reset stop projection 170. The patient then releases the lifting pressure and the hundreds counter wheel 163 with the attached gear teeth 167 is forced by the coiled compression spring 173 into the initial starting position ready to begin counting the medication doses for the replacement medication canister 13 seen in FIG. 8A.

FIGS. 9A–9D depict a ninth embodiment having both a disposable and a reusable two-wheeled counter system for substitution in the place of a three-wheeled counter system when a manufacturer's recommended number of "safe" doses of medication is less than "100". The counter wheel activator device can be either the external plunger-type trigger device 120 depicted in FIG. 8C or the lever-type trigger device 150 depicted in FIG. 7D. Construction can be either on the manufacturer's modified dispenser system 10 shown in FIG. 4C or on the slip-on counter sleeve device 100 shown in FIG. 2A.

Alternatively, as shown in FIG. 2A only, wherein the plunger-type trigger device 120 is employed, the contact-type adhesive 205 may be used to attach the independently constructed counter housing 213 and the support column 214 directly to either the dispenser system 10 or the counter sleeve device 100.

FIG. 9A depicts a front elevational view of a modified counter housing 113, the height of which is shortened when compared with the counter housing 113 in FIG. 8A, due to the removal of the hundreds counter wheel 163 and the dog 166 attached to the circumference of the tens counter wheel 162. Note that the hundreds counter wheel 163 and the dog 166 were required for the three-wheeled counter system previously depicted in FIGS. 7B and 8D.

Returning to FIG. 9A, the portal 160B displays the digit "8" in the tens position and the portal 160A displays the digit "0" in the units position representing a hypothetical "80" safe doses of medication contained in the medication canister 13.

FIG. 9B presents a front elevational view of the counter housing 113 with the cover 143, as seen in FIG. 9A, removed to expose the units driver counter wheel 161 and the tens counter wheel 162. The dog 164 is attached to the circumference of the units driver counter wheel 161 and is poised to engage one of the ten evenly spaced gear teeth 165 located on the circumference of the tens counter wheel 162. In dashed lines to indicate a hidden view, the counter wheel stop projection 168 is attached to the underside of the tens counter wheel 162 and the counter body stop projection 169 is attached to and rises vertically upwards from the floor 144 of the counter housing 113.

Continuing with FIG. 9B, the initial medication dose delivery begins with the patient depressing the medication canister 13 and activating either the exact same lever-type trigger device 150 with the attached dog-type drive head device 180 shown in FIG. 7D or the exact same plunger-type trigger device 120 with the attached dog-type drive head device 180 shown in FIG. 8C. This action results in the rotation of the units driver counter wheel 161 one-tenth of a revolution clockwise, thereby moving the "9" digit into the position previously occupied by the "0" digit. This same action also results in the dog 164, extending from the circumference of the units driver counter wheel 161, engaging one of the ten gear teeth 165 on the tens counter wheel 162 and thereby turning the engaged gear 165 one-tenth of a revolution counterclockwise. Consequently, the "7" digit on the face of the tens counter wheel 162 moves into the position previously occupied by the "8" digit. The portals 160A and 160B in FIG. 9A now display "79" safe doses of medication remaining in the medication canister 13.

Returning to FIG. 9B and also referring to FIG. 9A, at the completion of the delivery of 80 "safe" doses of medication, the units driver counter wheel 161 will have completed eight full revolutions clockwise and will display "0" in the units portal 160A. The tens counter wheel 162 will have completed eight partial revolutions counterclockwise and also will display "0" in the tens portal 160B. The counter wheel stop projection 168 will have moved clockwise into contact with the right side of the counter body stop projection 169, thereby "locking up" the dispenser system completely if an additional 81st medication dose delivery is attempted. Thereafter, either the manufacturer's dispenser system 10 along with the attached counter or the counter sleeve device 100 is replaced.

FIGS. 9C and 9D jointly depict a two-wheeled counter reset arrangement that closely resembles the reset construction previously depicted in FIGS. 7G and 7H and again in FIGS. 8E and 8F. As seen in FIG. 9C, the counter wheel stop projection 168 has moved counterclockwise and has contacted the counter body stop projection 169, thus locking up the counter and trigger system (not shown) completely so that further medication doses cannot be delivered. At this point, the portals 160A and 160B in FIG. 9A read "00".

Continuing with FIGS. 9C and 9D, modifications which allow for reset of the two-wheeled counter include the tapering of the counter housing 113 and the enlarging of the tens counter wheel 162 slightly in order to expose two edges of the tens counter wheel 162. This tens counter wheel 162 is moved further away from the units driver counter wheel 161 and the dog 164 is lengthened to compensate for the greater distance between the gear teeth 165 and also for the increased rotational distance required each time the tens counter wheel 162 is required to move. The counter reset stop projection 170, rising upwardly from the floor 144 of the counter housing 113, aids in the counter reset operation in the same manner as described in connection with FIGS. 7G and 7H. Further modifications include, as shown in FIG. 7H, the addition of the hollow cylindrical extension 174 to the cover 143 of the counter housing 113 to receive the shaft 175 of the tens counter wheel 162. As seen in FIG. 9D, this shaft 175 projects part way into the hollow cylindrical extension 174 and rests against the coiled compression spring 173 in the same manner as seen in FIG. 7H.

Resetting the counter involves several steps for this ninth embodiment. Initially, as seen in FIGS. 9C and 9D, the patient lifts the exposed portions of the tens counter wheel 162 against the pressure of the coiled compression spring 173 in order for the gear 165 to clear contact with the dog 164 attached to the underside of the units driver counter wheel 161. The tens counter wheel 162 is then turned clockwise with a series of repeated lifting and turning actions until the counter wheel stop projection 168 contacts the counter reset stop projection 170. The lifting pressure applied by the patient is then released and the tens counter wheel 162 drops into its original starting position due to the pressure exerted by the coiled compression spring 173. The digit "8" has now moved to the space previously occupied by the digit "0" and the counter wheels 161 and 162 are in position to begin a new count down of "80" medication doses contained in the replacement medication canister 13 of FIG. 9B.

FIGS. 10A–10E introduce a tenth embodiment in which the previously described plunger-type trigger 120 is utilized with a new pin-type drive head device 220 to activate a single-wheeled counter device. The pin-type drive head device 220 may also be interchanged with the dog-type drive head device 180 previously discussed in connection with the seventh and eighth embodiments shown in FIGS. 7D and 8C, respectively.

This single-wheeled counter device of FIGS. 10A–10E may be constructed as a part of either the manufacturer's dispenser system 10 or the "slip-on" counter sleeve device 100. Furthermore, this single-wheeled counter device may be either the disposable type or the reusable type, if the manufacturer offers replacement medication canisters 13.

Alternatively, as shown in FIG. 2A only, the independently constructed counter housing 213 and the support column 214 may be attached either to the dispenser system 10 or the counter sleeve device 100 by the contact-type adhesive 205.

FIG. 10A depicts a front elevational view of either the modified manufacturer's dispenser system 10 or the counter sleeve device 100 with the support column 114, the medication canister 13, and the plunger-type trigger 120 evident. The cover 143 of the counter housing 113 contains a pie-shaped portal 194 exposing a partially hidden counter wheel 191 set at a representative initial starting count of "40" safe medication doses indicated opposite a triangular pointer 193. A red warning zone is shown partially exposed on the face of the counter wheel 191. The function of this warning zone is discussed later in regard to FIG. 10D, along with the operation of the counter wheel stop projection 168 and the body stop projection 169 shown in phantom lines.

FIG. 10B depicts an enlarged partial side elevational view of a complete counter wheel activator system including the plunger-type trigger 120, the support column 114, the connecting box 187, the drive head connector 189, and the newly introduced pin-type drive head device 220. All sub-components not identified herein are constructed and operated in the same manner as those elements depicted in FIG. 8C showing the eighth embodiment.

Returning to FIG. 10B, one can see how the drive head connector 189 connects to the pin-type drive head device 220. A beveled drive pin 221 projects outwardly from the device 220 and rests against one of a plurality of gear teeth 192 cut into the back side of the counter wheel 191.

Referring to the enlarged view of details in FIG. 10C, the beveled drive pin 221, constructed with two keys 223, is installed in two key slots 224 extending partially into the drive head body 222 of the pin-type drive head device 220. While one end of the beveled drive pin 221 is free and extends out of the drive head body 222, the opposite end of the beveled drive pin 221 rests against a compressed coil spring 226. The outward movement of the beveled drive pin 221 is limited by the contact of the two keys 223 with an installed cap 225. The two keys 223 also provide for consistent alignment of the beveled drive pin 221 inside the drive head body 222 as well as for consistent alignment of the beveled drive pin 221 with the gear teeth 192 shown in FIG. 10B.

Continuing with FIG. 10B, the amount of clockwise movement of the counter wheel 191 and the amount of meshing of the beveled drive pin 221 with the gear teeth 192 are controlled by two structural variables. The first variable factor is the distance of the pin-type drive head device 220 from the center of the counter wheel 191. The greater the distance from the center, the less the counter wheel 191 moves for each downward movement of the pin-type drive head device 220. The second variable factor is the size of a pre-determined gap 190 between the bottom tip of the vertical trigger shaft 123 and the upper end of the drive head connector 189.

As the size of the gap 190 increases, the tip of the vertical trigger shaft 123 moves a greater distance downwardly before making contact with and moving the drive head connector 189 and the attached pin-type drive head device 220. This arrangement results in less downward movement of the pin-type drive head device 220 and reduces the clockwise movement of the counter wheel 191.

Continuing with FIG. 10B, to deliver the first medication dose, the patient depresses the concave disk 122 and the medication canister 13. This depressing action results in the vertical trigger shaft 123 moving downwardly, first closing the gap 190, then pushing the drive head connector 189 and the attached pin-type drive device 220 downwardly for the remainder of its travel. When the pin-type drive device 220 moves downwardly, the extended beveled drive pin 221 likewise moves downwardly against the gear 192 and rotates the counter wheel 191 one position clockwise.

Referring back to FIG. 10A, the count in the portal 194 will indicate a decrease in the number of safe medication doses remaining from "40" to an unidentified dashed mark representing "39", now opposite the triangular pointer 193. The counter wheel stop projection 168 likewise will have rotated one position clockwise.

Returning to FIG. 10B, upon the release of the patient-applied pressure, the concave disk 122 rises due to the upward movement of the medication canister 13 returning to its rest position, thereby raising the vertical trigger shaft 123 to its normal rest position. The drive head connector 189 also rises, due to the pressure of the contracting coil spring 188, until keys 186 reach the top end of the key slots 126. This action is possible because the coil spring 188 is attached at one end to the bottom of the drive head connector 189 and is attached at the other end to the bottom of the connecting box 187. The beveled drive pin 221, while moving upwardly, recedes into the drive head body 222 as it rides up the slope to the following gear tooth 192. Upon reaching the apex of the gear tooth 192, the beveled drive pin 221 suddenly moves outwardly due to the pressure applied by the compressed coil spring 226, thereby placing the beveled drive pin 221 in position again to turn the counter wheel 191 and to record the next medication dose delivery.

As depicted in FIGS. 10D and 10E, the counter wheel 191 becomes "locked up" after the delivery of 40 medication doses, as visually indicated by the digit "0" residing opposite the triangular pointer 193, and also as visually indicated by the highly noticeable red warning zone exposed in the right half of the portal 194. At this point, the counter wheel stop projection 168, initially in contact with the left side of the fixed counter body stop projection 169, has moved clockwise nearly one revolution and now rests in contact with the right side of the fixed counter body stop projection 169. Thus, the counter wheel 191 can no longer move clockwise and the entire counter system is "locked up".

Referring back to FIG. 10B, one sees that the pin-type drive device 220 and the drive head connector 189 can no longer move downwardly. The plunger-type trigger device 120 can move downwardly, but only a limited amount, depending on the size of the gap 190 employed for a specific numerical capacity of the counter wheel 191. The net result is that the medication canister 13, in contact with the underside of the concave disk 122, cannot be depressed to a point where it can dispense a forty-first dose of medication. The disposable dispenser system 10 and the counter sleeve 100, if utilized, are then discarded by the patient and replaced.

FIGS. 10D and 10E depict modifications to allow a patient to reset and reuse a single-wheeled counter after the previously described "lock-up" condition occurs. FIG. 10D depicts a front elevational view of the counter housing 113, the width of which has been decreased in order to expose two edges of the counter wheel 191. The results of the previously described "lock-up" condition are evidenced by the remaining dose count of "0" opposite the triangular pointer 193 and by the red warning zone now showing in the right half opening in the portal 194. The contact of the counter wheel stop projection 168 with the fixed counter body stop projection 169, as the immediate cause of the "lock-up" condition, is evident in hidden view, as well as in the side view of FIG. 10E.

Continuing with FIG. 10E, another modification of this tenth embodiment is a hollow cylindrical extension 195 which is added to the cover 143 of the counter housing 113. A shaft 196 of the counter wheel 191 extends into the hollow cylindrical extension 195 and rests against a coiled spring 197.

Returning to FIG. 10D and also continuing with FIG. 10E, to reset the counter wheel 191 to the initial starting number of "40" doses, the patient utilizes a thumb and an index finger to lift the counter wheel 191 in order to raise the counter wheel stop projection 168 clear of the counter body stop projection 169. Referring back to FIG. 10B, one sees that this lifting action also raises the gear teeth 192 clear of the beveled drive pin 221.

Returning to FIGS. 10D and 10E, the patient then turns the counter wheel 191 clockwise for a short distance, lines up the count of "40" with the triangular pointer 193, and then releases the counter wheel 191 so that the wheel 191 is now forced into its original starting position due to the pressure applied by the coil spring 197 pushing outwardly on the end of the shaft 196.

Referring to FIG. 10A, the counting system is now ready to record doses dispensed either from a replacement medication canister 13 installed within the existing dispenser system 10 or from the existing slip-on counter sleeve device 100 attached to a new dispenser system 10.

FIGS. 11A–11E introduce an eleventh embodiment in which the lever-type trigger device 150 and the pin-type drive head device 220 attached thereto are utilized in conjunction with the manufacturer's modified dispenser system 10 to activate a single-wheeled mechanical counter device similar to the type shown in FIG. 10. Practically all of the construction and operations involved herein have been depicted and discussed previously with respect to FIGS. 2A–10E that will be referenced whenever necessary.

FIG. 11A depicts a front elevational view of the manufacturer's modified dispenser system 10 including the attached counter housing 113 with the cover 143 containing the portal 194 through which the clockwise rotating counter wheel 191 is exposed. The face of the counter wheel 191 contains numerical digits representing the number of safe doses remaining in the pressurized medication canister 13. The representative starting safe medication dose of "40" is indicated on the counter wheel 191, as seen through the portal 194 opposite the triangular pointer 193. The red warning zone is also partially evident in the portal 194. In hidden view, there is shown by the phantom lines the counter wheel stop projection 168 attached to the reverse face of the counter wheel 191. The wheel stop projection 168 is also shown in the starting position in contact with the left side of the counter body stop projection 169 which rises vertically from the floor 144 of the counter housing 113. Also, in phantom lines to indicate a hidden view, there are the lever-type trigger device 150, the vertical shaft extension 182, and the attached pin-type drive head device 220 which turns the counter wheel 191 the equivalent of one digit clockwise each time that the canister 13 is depressed to dispense medication. Offsetting the lever-type trigger device 150 from the center of the counter wheel 191 is one method of controlling the clockwise rotation necessary for various dose count totals. In other words, the farther the offset from the center, the less the counter wheel 191 moves incrementally and vice versa. Referring to FIG. 11B, the other method of controlling the clockwise rotation of the counter wheel 191 is to change the length of the external leg of the lever-type trigger device 150. In other words, the shorter the external leg of the device 150, the less upward movement results for each depression of the medication canister 13 and vice versa.

FIG. 11B depicts an enlarged side elevational view of details of the lever-type trigger device 150, originally described in detail in connection with FIG. 7D where it was shown to be operated with the attached dog-type drive head device 180. Returning to FIG. 11B, the dog-type drive head device 180 has been replaced with a pin-type drive head device 220, the construction of which is detailed in FIG. 11C. Continuing with FIG. 11C, the drive head body 222 of the pin-type drive head device 220 is constructed with a hollow keyed opening 224 to receive the beveled drive pin 221 with two attached keys 223. The inner end of the beveled drive pin 221 rests against the coil spring 226 that compresses when the beveled drive pin 221 moves inwardly. Outward movement of the beveled drive pin 221 is limited due to the contact of the two keys 223 with the installed cap 225. The two keys 223 also provide the beveled drive pin 221 with stability during operation. Returning to FIG. 11B, while at rest, the extended beveled drive pin 221 remains in contact with one of the gear teeth 192 cut into the back side of the counter wheel 191.

The operation of this eleventh embodiment will now be described with initial reference to FIGS. 11A and 11B. During the dispensing of the initial medication dose, the patient depresses the canister 13, moving the metal sealing ring 154 downwardly against the internal leg of the lever-type trigger device 150. This movement causes the external leg of the lever-type trigger device 150, the shaft extension 182, and the attached pin-type drive head device 220 to move upwardly, thus causing the beveled drive pin 221 to move the gear tooth 192 and to rotate the counter wheel 191 one position clockwise. Referring to FIG. 11A, this movement results in the unidentified dashed mark representing "39" rotating clockwise to replace the original digit "40" opposite the triangular pointer 193. This rotational action also results in the attached counter wheel stop projection 168 moving one position clockwise. Returning to FIG. 11B, at the end of the dispensing of the initial medication dose, the patient releases his or her finger pressure, thus allowing the medication canister 13 and the attached sealing ring 154 to rise to the normal rest position. The coil-type spring 155 exerts a downward pressure on the external leg of the lever-type trigger device 150, thereby causing the internal leg to move upwardly and to remain in continuous contact with the underside of the sealing ring 154. Conversely, the external leg of the lever-type trigger device 150, the shaft extension 182, and the attached pin-type drive head device 220 move downwardly, thus causing the beveled drive pin 221 to recede into the drive head body 222 and to compress the coil spring 226 as the beveled drive pin 221 rides down the slope to the next gear tooth 192. Upon reaching the next gear tooth 192, the beveled drive pin 221 is moved outwardly due to the pressure applied by the compressed coil spring 226 and is now ready for the next medication dose to be dispensed. Routine removal and replacement of the medication canister 13 for maintenance will not affect adversely the existing alignment of the beveled drive pin 221 with the gear tooth 192. The lever trigger stop 158 restricts the downward movement of the external leg of the lever-type trigger device 150 which would normally continue to move downwardly due to the pressure applied by the coil-type spring 155. The unrestricted downward movement of the external leg of the lever-type trigger device 150 could result in a possible miscount due to one or more gear teeth 192 being skipped if the lever trigger stop 158 is not used.

Referring back to FIG. 11A, "lock-up" of the counter wheel 191 occurs after 40 safe doses of medication are delivered and the counter wheel stop projection 168 has rotated clockwise into contact with the right side of the counter body stop projection 169. Moving to FIG. 11B, a 41st dose of medication cannot be dispensed because the external leg of the lever-type trigger device 150 and the attached pin-type drive head device 220 can no longer move upwardly and thus cannot turn the counter wheel 191 clockwise, nor can the internal leg of the lever-type trigger device 150, in contact with the bottom of the sealing ring 154, move downwardly. As a consequence of the "lock up" of the counter wheel 191, the medication canister 13 will no longer move downwardly as a result of patient-applied pressure to the top thereof. The complete dispenser system 10 and the counter device are then replaced.

FIGS. 11D and 11E jointly depict minor modifications of the eleventh embodiment to allow for a single-wheeled counter to be reset and reused after the previously described "lock-up" condition occurs for the counter wheel 191. FIG. 11D depicts a front elevational view of the counter housing 113, the width of which has been decreased in order to expose two edges of the counter wheel 191. The digit "0" is opposite the triangular pointer 193 and a red warning zone fills the right half of the portal 194. The contact of the counter wheel stop projection 168 with the fixed counter body stop projection 169, which contact is the cause of the "lock-up" condition for the counter wheel 191, is evident in hidden view as well as in the side view of FIG. 11E.

Continuing with FIG. 11E, another modification of the eleventh embodiment is the addition of the hollow cylindrical extension 195 to the cover 143 of the counter housing 113. The shaft 196 of the counter wheel 191 extends into the cylindrical extension 195 and rests therein against the coiled spring 197.

Returning to FIG. 11D, to reset the counter, the patient lifts the counter wheel 191 to raise the counter wheel stop projection 168 over the counter body stop projection 169. Referring back to FIG. 11B, one can see that the lifting action also raises the gear teeth 192 over the constrained beveled drive pin 221. Returning to FIG. 11D, the patient then turns the counter wheel 191 clockwise, lines up the digit "40" with the triangular pointer 193, and then releases the counter wheel 191 which now drops into its original starting position, ready to record the number of safe medication doses dispensed from the replacement canister 13 shown in FIG. 11A.

FIGS. 12A–15 depict three methods of attaching the counter devices directly onto a manufacturer's medication dispenser system 10. The counting devices, which record the number of medication doses dispensed, are user-activated and operate in conjunction with, but are independent of, the actual dispensing of the medication. The counting devices, with either minor changes in or deletion of various components, are constructed and operated in the same manner as those devices described in the preceding 11 embodiments covering FIGS. 2A–11E.

To refresh the reader's recollection, the counter housing 113, first identified in FIG. 2A, was constructed as part of the slip-on counter sleeve device 100 and, again identified in FIG. 4B, was constructed as part of the manufacturer's modified dispenser system 10. In FIGS. 12A–12D, the contents of an independently constructed counter housing 213 include the electronic counter device 130, first generally identified in FIG. 2D and again identified in schematic detail in FIGS. 5A and 5C.

FIG. 12A depicts a front elevational view of the twelfth embodiment in which a counter housing 213 is mounted, for example, on the front face of the dispenser body 12 of the manufacturer's dispenser system 10. In FIG. 12A, there are illustrated the following: the LCD counter display 131, the general location of the electronic counter device 130, the count reset microswitch 139, and the relocated dose count microswitch 135 extending outwardly through a water tight opening located on the top of the counter housing 213. An attachment bar 201 is constructed as part of each side wall of the counter housing 213 to which an expandable strap 202 is attached to secure the counter housing 213 to the dispenser body 12.

FIG. 12B depicts a top plan view of the twelfth embodiment and details the first method of attaching the counter housing 213 to the dispenser body 12. The rear outside wall 212 of the counter housing 213 is contoured to match an exterior outside wall of the dispenser body 12 at an intended point of mounting. Two external attachment bars 201, also shown in FIG. 12A, each receive a pair of hook clasps 203 connected to the expandable strap 202. When stretched around the dispenser body 12, the strap 202 supplies sufficient pressure to create the necessary friction to hold the counter housing 213 in position. Installation of the counter housing 213 involves the user grasping the dispenser body 12 with fingers of one hand while holding the counter housing 213 in place with the thumb of the same hand. With the other hand, the user attaches the first hook clasp 203 to one of the two attachment bars 201, then stretches the strap 202 around the dispenser body 12, and connects the second hook clasp 203 to the other of the two attachment bars 201.

FIG. 12C depicts an enlarged top plan view of the twelfth embodiment and a second method of attaching the counter housing 213 to the dispenser body 12. The contact-type adhesive 205, initially shown in FIG. 2A, is applied to the contoured rear outside wall 212 of the counter housing 213. If attached by the manufacturer, the counter housing 213 is placed directly onto an outside wall of the dispenser body 12 for a permanent installation. If attached by the user, the contact-type adhesive 205 is covered with a plastic film 206. Upon receipt, the user peels off the plastic film 206, then presses the contact-type adhesive 205 against the dispenser body 12 at a predesignated location, thereby effecting a permanent installation.

FIG. 12D depicts an enlarged top plan view of the twelfth embodiment and a third method of attaching the counter housing 213 to the dispenser body 12. This method utilizes a self-adhering, pre-sized VELCRO® brand hook and loop fastener. Installation is carried out by removing the plastic film 206 (not shown in FIG. 12D) covering the contact-type adhesive 205 (also not shown in FIG. 12D) located on the back of a loop-type component strip 207, then pressing the strip 207 onto the outside wall of the dispenser body 12 at a designated location. The plastic film 206 (not shown) is then removed from the back of a hook-type component strip 208 and the adhesive side of the strip 208 is applied to the contoured rear outside wall 212 of the counter housing 213 and pressed into place. The placing of the hook-type component strip 208 in contact with the loop-type component strip 207 completes the installation cycle. An additional supply of self-adhering loop-type component strips 207 allows the user to transfer the counter housing 213 to multiple replacement dispenser systems 10 if the electronic counting device 130 shown in FIG. 12A is intended for reuse.

Continuing with FIG. 12A, activation of the electronic counter device 130 is done by the user placing the thumb on the underside of the counter housing 213 and the index finger on the top of the counter housing 213. Then, the user presses downwardly on the dose count microswitch 135 with the index finger, thereby closing the microswitch 135 and effecting a reduction of "1" from the number of safe doses of medication shown by the LCD counter display 131. The user then releases the finger pressure and notes the number of safe doses remaining as indicated on the LCD counter display 131. If either at least "1" dose remains or if the LCD counter display 131 blinks "000" off and on for a preprogrammed number of times, e.g. ten, the user proceeds with the dispensing of either the next or the last safe medication dose, as shown in FIG. 1C.

Returning to FIG. 12A, if the user notes a permanent nonblinking display of "000" on the LCD counter display 131 indicating no safe doses remaining, and the manufacturer's dispenser system 10 is intended for a single cycle use only, then the complete dispenser system 10, the counter housing 213, and the contained electronic counter device 130 are discarded. If the electronic counter device 130 is intended for reuse, i.e. replacement medication canisters 13 are available, the count reset switch 139, installed through a water tight seal in the right side wall of the counter housing 213, is operated. To operate the count reset switch 139, the user places the thumb on the opposite left side wall of the counter housing 213, presses inwardly on the count reset switch 139 with the index finger, and then releases the finger. This action will reset the LCD counter display 131 to the original starting count as depicted in FIG. 5C. The user will then either replace the medication canister 13 and begin a new countdown sequence or reattach the existing counter housing 213 with the enclosed electronic counter device 130 on a manufacturer's new dispenser system 10. FIGS. 5A and 5C are detailed schematic drawings of the electronic counter device 130, its components, advantageous features, and user-operating procedures.

Figure 13A:
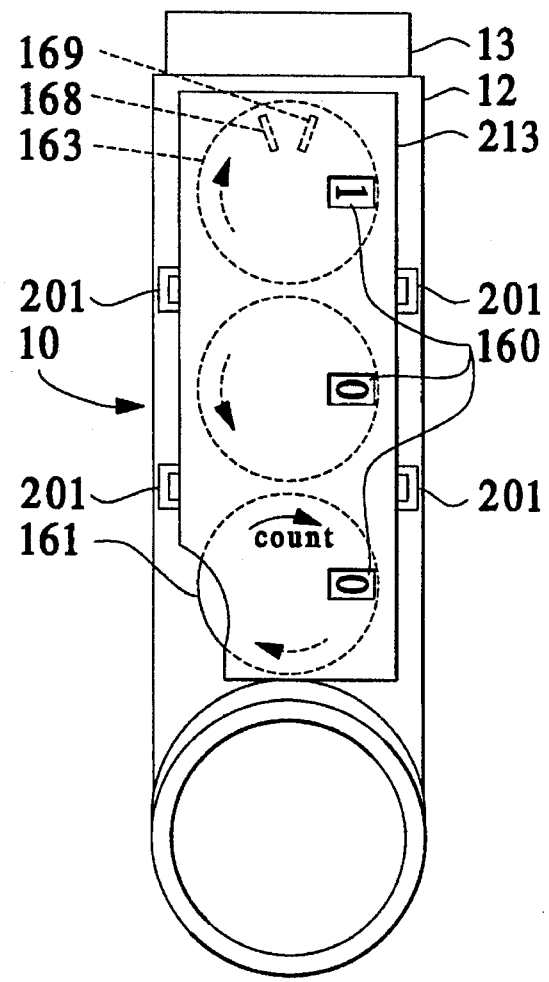
FIG. 13A is a front elevational view of a thirteenth embodiment.
Figure 13B:
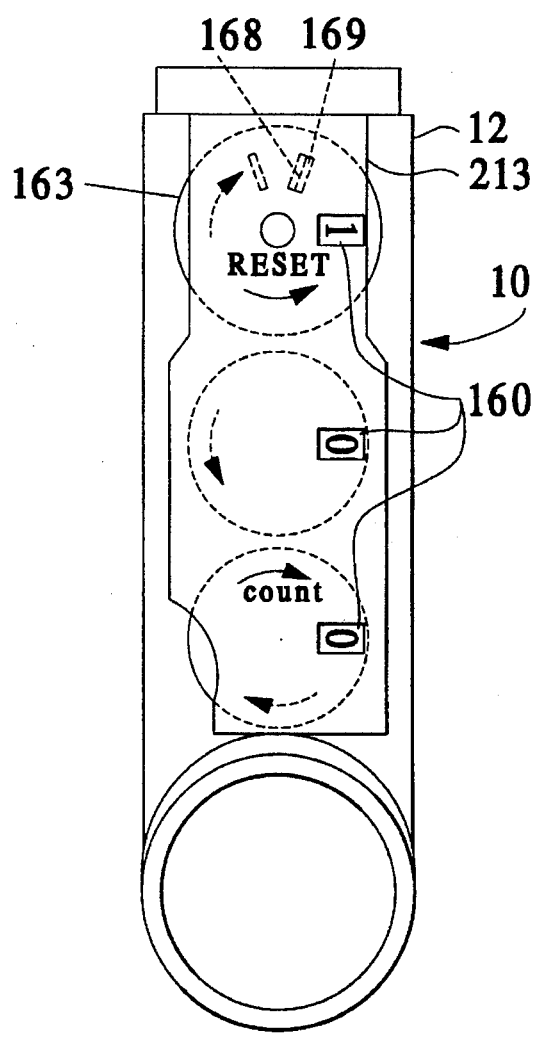
FIG. 13B is a front elevational view of a modified thirteenth embodiment having a reset feature.

FIGS. 13A and 13B depict the mounting and operating procedures for two independently, user-activated, three-wheeled, disposable and reusable counting systems. FIG. 13A depicts a front elevational view of a thirteenth embodiment of the disposable counter housing 213 being mounted on an exterior wall of the dispenser body 12 and containing the three-wheeled counter system first depicted in FIG. 7B. FIG. 7B showed the interaction of the three counter wheels, gears and dogs necessary to record each medication dose delivery. FIG. 7B also showed the structural arrangement resulting in counter "lock-up" wherein the units drive counter wheel 161 cannot be moved clockwise after dispensing the limit of a manufacturer's identified safe doses contained in the medication canister 13.

In FIG. 13A, the counter housing 213 is cut inwardly on the lower left side to expose a portion of the units drive counter wheel 161. The cut-out portion allows the user to manually turn the units counter drive wheel 161 clockwise one digit with a finger or thumb prior to delivering a dose from the medication canister 13. This action reduces the count in the portals 160 by "1".

Returning to FIG. 7B in reference to FIGS. 13A and 13B, after the total number of safe doses of medication are dispensed, for example "100", the counter wheel stop projection 168 on the back of the hundreds counter wheel 163 will be in contact with the body stop projection 169. As shown in FIG. 7B, the user will be unable to turn the units driver counter wheel 161 clockwise any farther with the finger, thereby reinforcing the visual reading of "000" safe doses remaining, as indicated in the portals 160 in FIG. 13A. Thereafter, the disposable dispenser system 10 and the attached counter housing 213 with its contents are discarded.

FIG. 13B depicts a front elevational view of a modified thirteenth embodiment of the reusable counter housing 213 containing the three-wheeled counter system first depicted in FIGS. 7G and 7H. The counter housing 213 is attached to the outside wall of the manufacturer's dispenser body 12 utilizing one of the three methods depicted in FIGS. 12B, 12C or 12D. The counter housing 213 is cut inwardly on the lower left side to expose a portion of the units drive counter wheel 161 in a manner similar to FIG. 13A. Also, the upper end of the counter housing 213 is tapered inwardly on two sides to expose the hundreds counter wheel 163 in a manner similar to FIG. 7G. Returning to FIG. 13B, the user turns the exposed units drive counter wheel 161 clockwise with either a finger or a thumb prior to the delivery of each dose from the medication canister 13. This action and succeeding manual actions reduce the count of remaining safe doses of medication indicated in the portals 160 until "000" is displayed and counter "lock-up" occurs. The detailed illustration of counter "lock-up", wherein the counter wheel stop projection 168 contacts the body stop projection 169, and the operation of the counter reset feature are shown in FIGS. 7G and 7H.

FIG. 13A depicts a front elevational view of the first method of attaching the counter housing 213, having the three-wheeled disposable and reusable counter system, to the manufacturer's dispenser body 12. There are four attachment bars 201 with two attached to either side of the counter housing 213 for stability due to the size of the counter housing 213. Two stretchable bands 202 with attached hook clasps 203, normally connected to the four attachment bars 201, are not shown. Refer to FIG. 12A and 12B for construction and installation details relating to the bands 202 and the hook clasps 203. Refer to FIG. 12C for a second method of attachment utilizing adhesives. Refer to FIG. 12D for a third method of attachment utilizing a hook and loop fastener.

Figure 14B:
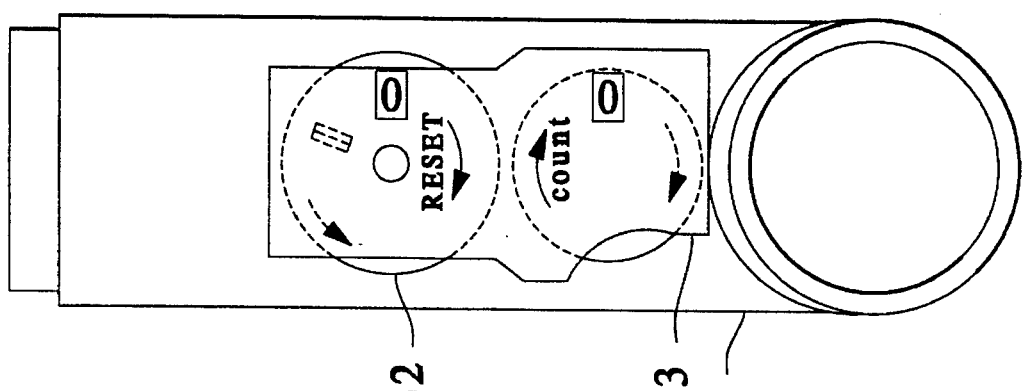
FIG. 14B is a front elevational view of a modified fourteenth embodiment having a reset feature.
Figure 14A:
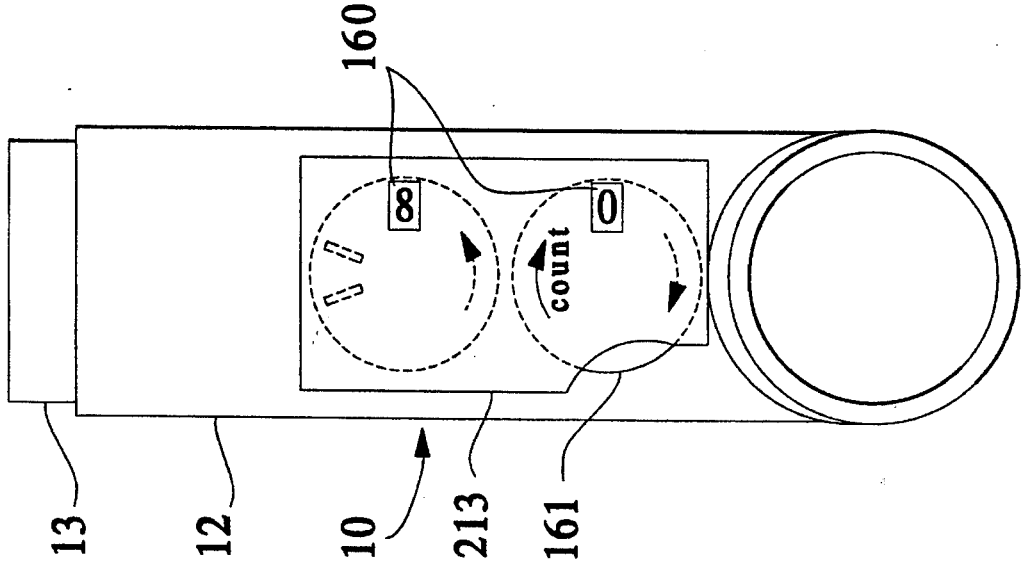
FIG. 14A is a front elevational view of a fourteenth embodiment.

FIGS. 14A and 14B, respectively, depict front elevational views of a fourteenth embodiment and a modified fourteenth embodiment of a manually operated, disposable and reusable, two-wheeled counter system first identified in FIGS. 9A–9D.

In FIG. 14A, a disposable two-wheeled, manually operated, counter system is contained in a counter housing 213 that is attached to the dispenser body 12 of the manufacturer's dispenser system 10. A lower left portion of the counter housing 213 is cut back to expose a portion of the units driver counter wheel 161. The user activates the counter system by first rotating the units driver counter wheel 161 clockwise with a finger or thumb prior to dispensing a dose from the medication canister 13. The mechanical counting process leading to eventual counter "lock-up" was depicted in FIGS. 9A and 9B. Returning to FIG. 14A, the counter housing 213 and the contained two-wheeled counter system, as well as the dispenser system itself, are discarded after the count in the portals 160 reaches "00".

FIG. 14B depicts a modified fourteenth embodiment including a reusable two-wheeled counter system with the counter housing 213 being attached to the manufacturer's dispenser body 12. A portion of the counter housing 213 is cut away to allow the user to activate the countdown in the same manner as shown in FIG. 14A. An upper portion of the counter housing 213 is tapered inwardly to expose two sides of the tens counter wheel 162 in the same manner shown in FIG. 9C. The construction and operation of the counter reset, after counter "lock-up" has occurred, was depicted in FIGS. 9C and 9D.

The attachment of both the disposable counter system shown in FIG. 14A and the reusable counter system shown in FIG. 14B with the two-wheeled counter housing 213 being connected onto the manufacturer's dispenser body 12 utilizing the stretchable band 202 was depicted in FIG. 12B. Attachment utilizing contact-type adhesives was depicted in FIG. 12C, while the use of a hook and loop fastener was depicted in FIG. 12D.

Figure 15:
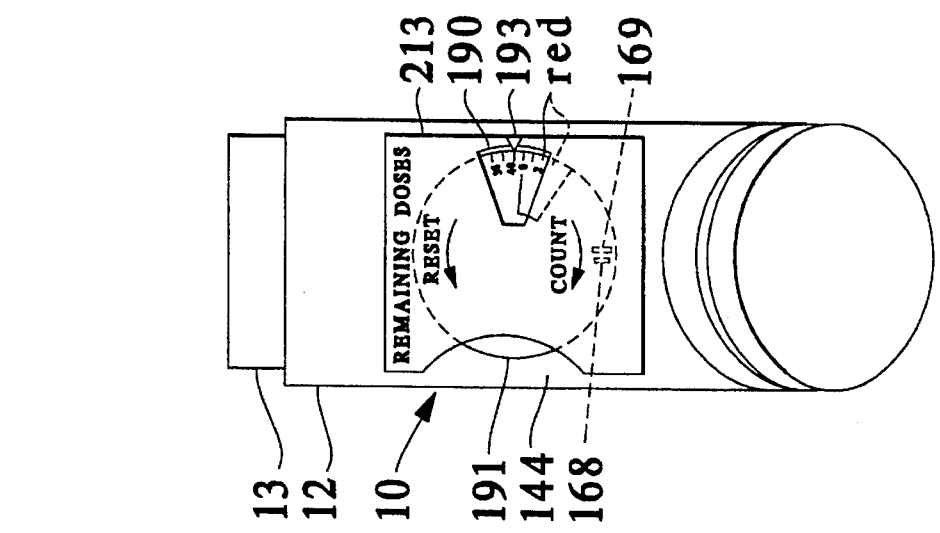
FIG. 15 is a front elevational view of a fifteenth embodiment having a reset feature.

FIG. 15 depicts a user-actuated, single-wheeled counter device which is a fifteenth embodiment having the counter housing 213 mounted on the manufacturer's dispenser body 12. The single-wheeled counter device was first depicted in FIG. 10A wherein the construction and operations were shown. The elimination of the automated plunger-type trigger device 120 and its related components depicted in FIG. 10B from this fifteenth embodiment allows for a single construction to function in both the disposable and the reusable mode.

Returning to FIG. 15, a portion of the left side of the counter housing 213 is removed to expose a portion of the counter wheel 191. Prior to dispensing a dose from the medication canister 13, the user moves the counter wheel 191 clockwise with a finger or thumb to reduce the count displayed in the portal 190 opposite to the triangular pointer 193, by one digit. For the initial dose of medication, the thirty-ninth dashed line replaces the number "40" opposite the triangular pointer 193. At the same time, the counter wheel stop projection 168, attached to the underside of the counter wheel 191, moves clockwise away from the left side of the counter body stop projection 169 that rises upwardly from the floor 144 of the counter housing 213. At the completion of "40" doses of medication, the digit "0" appears opposite the triangular pointer 193 and the lower half of the portal 190 displays a red zone as an additional warning of the need for a replacement medication canister 13. The counter wheel stop projection 168 will have moved clockwise almost one full revolution and will be in contact with the right side of the counter body stop projection 169. The user is unable to turn the counter wheel 191 clockwise any further, signifying that the total number of manufacturer-designated safe doses of medication in the canister 13 have been dispensed. If the single-wheeled counter system either is to be reused with a new replacement medication canister 13 or is to be transferred to a new dispenser system 10 as previously depicted in FIGS. 12B and 12D, the user turns the counter wheel 191 counterclockwise with a finger or thumb until the wheel counter stop projection 168 returns almost one full revolution to its original starting position and is again in contact with the left side of the counter body stop projection 169. The counterclockwise movement also places the original safe dose count of "40" for the new medication canister 13 opposite to the triangular pointer 193 next to the portal 190. The single-wheeled counter system is now ready to commence a new countdown sequence.

Attachment of the single-wheeled counter housing 213 to the manufacturer's dispenser body 12 with the stretchable strap 202 was depicted in FIG. 12B. Attachment utilizing the contact-type adhesive 205 was depicted in FIG. 12C while attachment with the hook and loop fastener was illustrated in FIG. 12D.

To summarize the invention, the dispenser system 10 delivers a number of safe doses from the pressurized and metered medication canister 13 via the dispenser body 12 to a patient. The improvement includes either the electronic counter device 130 or one of the wheeled mechanical devices for accurately determining the number of safe doses delivered from the medication canister 13. Also, a warning device alerts the patient either by a visual signal via electronic and mechanical devices, or by an audible signal via an electronic device, or by a tactile signal via a mechanical device, or by a combination of such signals, about an impending and then a final exhaustion of the number of safe doses delivered from the medication canister 13. Essentially, the improved system takes advantage of the patient-actuated movement of the medication canister 13 in the dispenser body 12 to activate either the electronic counter device 130 or one of the mechanical counter devices.

Alternatively, the counter device may be independently activated by the patient during the course of delivering a self-administered medication dose.

The foregoing preferred embodiments are considered to be illustrative only. Numerous other modifications and changes will readily occur to those persons skilled in the medical arts after reading this disclosure. Consequently, the disclosed invention is not limited to the exact devices shown and described above, but rather is encompassed within the letter and the spirit of the following claims.

What we claim as our invention is:

1. A system for delivering a number of safe doses of respiratory medication to a patient from a pressurized and metered medication canister mounted inside a manufacturer's dispenser body having a noncounting dispenser, wherein the system comprises:

(a) a removable sleeve adapted to be easily slipped onto and off the manufacturer's dispenser body without requiring reconstruction of the manufacturer's dispenser body, said sleeve having inner dimensions conforming to outer dimensions of the manufacturer's dispenser body;

(b) means, connected only to an outer side of the sleeve, for counting accurately the number of safe doses delivered from the medication canister to the noncounting dispenser;

(c) means, also connected to the outer side of the sleeve, for informing the patient about the number of safe doses remaining in a medication canister for delivery; and (d) an external plunger-type trigger rod means, carried by the sleeve, for activating automatically the counting means when the trigger rod means is depressed;

said counting means being simultaneously activated when a medication canister is depressed.

2. A system according to claim 1, further comprising:

(e) means for attaching the counting means to the sleeve.

3. A system according to claim 1, wherein:

said counting means is formed integrally with the sleeve.

4. A system according to claim 1, wherein:

said informing means includes a buzzer means for sending an audible signal indicating that a safe dose of respiratory medication has been delivered to the patient and also for sending an increased number of audible signals advising the patient that final exhaustion of the number of safe doses is imminent.

5. A system according to claim 4, wherein:

said informing means includes a liquid crystal display means for showing a remaining dose count, for sending a blinking visual signal indicating the safe dose of respiratory medication is delivered to the patient and for sending an increased number of blinking visual signals to advise the patient of an impending and then final exhaustion of the number of safe doses.

6. A system according to claim 5, wherein:

said electronic counter includes a first internal microswitch means for recording a dose count on the liquid crystal display means and also includes a second external microswitch means for resetting the remaining dose count on the liquid crystal display means.

7. A system according to claim 1, wherein:

said counting means carries an electronic counter.

8. A system according to claim 7, wherein:

said electronic counter includes a programmed microcontroller and a replaceable power source.

9. A system according to claim 1, wherein:

a color of the sleeve matches a color of the manufacturer's dispenser body.

10. A system according to claim 1, wherein:

said counting means is preassembled and requires no adjustment by the patient when the sleeve is slipped onto and off the manufacturer's dispenser body.

11. A system according to claim 2, wherein:

said attaching means is removable and includes hook and loop fasteners.

12. A system according to claim 1, further comprising:

(f) lockout means for preventing false counts when the metered medication canister is either installed or removed from inside the manufacturer's dispenser body.

13. A system according to claim 12, wherein:

said sleeve remains in place when the metered medication canister is either installed or removed from inside the manufacturer's dispenser body.

14. A system for delivering a number of safe doses of respiratory medication to a patient from a pressurized and metered medication canister mounted inside a manufacturer's dispenser body having a noncounting dispenser, said system including means for counting accurately the number of safe doses delivered from the medication canister, means for informing the patient about the number of safe doses remaining in the medication canister, and an external plunger-type trigger rod means for activating automatically the counting means when the trigger rod means is depressed, wherein the improvement comprises:

a removable sleeve adapted to be easily slipped onto and off the manufacturer's dispenser body without requiring reconstruction of the manufacturer's dispenser body, said sleeve having inner dimensions conforming to outer dimensions of the manufacturer's dispenser body, said counting means being connected only to an outer side of the sleeve, said informing means also being connected to the outer side of the sleeve, and said trigger rod means being carried by the sleeve;

said counting means being activated by a depression of a medication canister inside the manufacturer's dispenser body.

* * * * *

UNITED STATES PATENT AND TRADEMARK OFFICE
CERTIFICATE OF CORRECTION

PATENT NO. : 5,564,414
DATED : October 15, 1996
INVENTOR(S) : William F. Walker et al.

It is certified that error appears in the above—identified patent and that said Letters Patent is hereby corrected as shown below:

On the cover page, left column, in section [56], after the last line, add the following:

| | | | |
|---|---|---|---|
| 2,613,108 | 10/1952 | Kraus | 222/647 |
| 2,967,643 | 1/1961 | Edelstein et al. | 222/647 |
| 2,971,382 | 2/1961 | Harris | 222/645 |
| 3,119,557 | 1/1964 | Chapman | 222/36 |
| 3,199,732 | 8/1965 | Strachan | 222/645 |
| 3,228,609 | 1/1966 | Edelstein et al. | 222/647 |
| 3,732,509 | 5/1973 | Florant et al. | 222/645 |
| 5,221,024 | 6/1993 | Campbell | 221/3 |
| 5,411,173 | 5/1995 | Weinstein | 222/162 |
| 5,421,482 | 6/1995 | Garby et al. | 222/162 |

On the cover page, right column, after FOREIGN PATENT DOCUMENTS but before line 1, add the following:

| | | | |
|---|---|---|---|
| 625,751 | 8/1961 | Canada | 222/645 |

UNITED STATES PATENT AND TRADEMARK OFFICE
CERTIFICATE OF CORRECTION

PATENT NO. : 5,564,414
DATED : October 15, 1996
INVENTOR(S) : William F. Walker et al.

It is certified that error appears in the above—identified patent and that said Letters Patent is hereby corrected as shown below:

Column 8, line 7, change "is" to --comprise--;

line 17, change "is" to --comprise--; and line 66, delete "0".

Column 13, line 41, after "7F", insert a comma.

Column 16, line 12, correct the spelling of "connector";

line 14, delete "("; and line 26, after "device", insert --180--.

Column 28, line 13, "are" should be --is--.

Signed and Sealed this

First Day of April, 1997

Attest:

BRUCE LEHMAN

Attesting Officer

Commissioner of Patents and Trademarks